US009307981B2

(12) United States Patent
Mikkaichi et al.

(10) Patent No.: US 9,307,981 B2
(45) Date of Patent: Apr. 12, 2016

(54) METHOD FOR SUTURING A GASTRIC WALL

(71) Applicant: OLYMPUS MEDICAL SYSTEMS CORP., Tokyo (JP)

(72) Inventors: Takayasu Mikkaichi, Tokyo (JP); Kunihide Kaji, Tokyo (JP); Takayuki Suzuki, Kanagawa-ken (JP); Takahiro Kogasaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 38 days.

(21) Appl. No.: 14/172,290

(22) Filed: Feb. 4, 2014

(65) Prior Publication Data

US 2014/0155915 A1 Jun. 5, 2014

Related U.S. Application Data

(62) Division of application No. 11/965,243, filed on Dec. 27, 2007, now abandoned.

(60) Provisional application No. 60/877,517, filed on Dec. 28, 2006, provisional application No. 60/898,309, filed on Jan. 30, 2007.

(51) Int. Cl.
*A61B 17/04* (2006.01)
*A61B 17/00* (2006.01)
(Continued)

(52) U.S. Cl.
CPC ....... *A61B 17/0469* (2013.01); *A61B 17/00234* (2013.01); *A61B 17/0482* (2013.01);
(Continued)

(58) Field of Classification Search
CPC ........... A61B 17/0469; A61B 17/0483; A61B 17/04; A61B 17/0491; A61B 17/00234; A61B 17/0482; A61B 17/062; A61B 17/0625; A61B 17/1114; A61B 2017/0498; A61B 2017/00827; A61B 2017/06076; A61B 2017/061; A61B 2017/06171; A61B 2017/00292; A61B 2017/306; A61F 5/0083; A61F 5/0076; A61F 5/0003; A61F 5/0089; A61F 5/0036; A61F 5/0069; A61F 5/0013
See application file for complete search history.

(56) References Cited

U.S. PATENT DOCUMENTS 5,041,085 A  8/1991 Osborne et al.
5,419,764 A  5/1995 Roll
(Continued)

FOREIGN PATENT DOCUMENTS

AU  2006230695 A1  11/2006
CN  2619592 Y  6/2004
(Continued)

OTHER PUBLICATIONS

European Search Report dated Feb. 24, 2011 issued in related Application No./Patent No. 10013468.3-1269 / 2263555.
(Continued)

*Primary Examiner* — Christopher L Templeton
(74) *Attorney, Agent, or Firm* — Scully, Scott, Murphy & Presser, P.C.

(57) ABSTRACT

A method for suturing a gastric wall including: inserting a flexible elongated loop-forming member perorally into a stomach; advancing the loop-forming member along a lesser curvature line of the stomach to contact with the gastric wall in vicinity of the pyloric antrum, such that the loop-forming member returns along a greater curvature line of the stomach to a predetermined position and connects to a distal end portion of an overtube to form a closed loop in the stomach; suctioning air from the stomach after forming the closed loop such that an anterior gastric wall is in proximity with a posterior gastric wall within a region encircled by the closed loop; and suturing at least a portion of the anterior gastric wall to the posterior gastric wall that are in proximity in the region encircled by the closed loop.

10 Claims, 33 Drawing Sheets

(51) Int. Cl.
*A61B 17/062* (2006.01)
*A61B 17/11* (2006.01)
*A61F 5/00* (2006.01)
*A61B 17/06* (2006.01)
*A61B 17/30* (2006.01)

(52) U.S. Cl.
CPC ......... *A61B17/0625* (2013.01); *A61B 17/1114* (2013.01); *A61B 17/0401* (2013.01); *A61B 17/0483* (2013.01); *A61B 2017/00292* (2013.01); *A61B 2017/00827* (2013.01); *A61B 2017/0443* (2013.01); *A61B 2017/0458* (2013.01); *A61B 2017/0464* (2013.01); *A61B 2017/0496* (2013.01); *A61B 2017/0498* (2013.01); *A61B 2017/061* (2013.01); *A61B 2017/06076* (2013.01); *A61B 2017/06171* (2013.01); *A61B 2017/1142* (2013.01); *A61B 2017/306* (2013.01); *A61F 5/0003* (2013.01); *A61F 5/0013* (2013.01); *A61F 5/0036* (2013.01); *A61F 5/0069* (2013.01); *A61F 5/0076* (2013.01); *A61F 5/0083* (2013.01); *A61F 5/0089* (2013.01)

(56) References Cited

U.S. PATENT DOCUMENTS

| | | | |
|---|---|---|---|
| 5,787,897 A | 8/1998 | Kieturakis | |
| 5,947,983 A * | 9/1999 | Solar et al. | 606/144 |
| 6,159,146 A | 12/2000 | El Gazayerli | |
| 6,332,880 B1 | 12/2001 | Yang et al. | |
| 6,872,214 B2 | 3/2005 | Sonnenschein et al. | |
| 7,083,629 B2 | 8/2006 | Weller et al. | |
| 7,306,614 B2 | 12/2007 | Weller et al. | |
| 7,530,984 B2 | 5/2009 | Sonnenschein et al. | |
| 7,571,729 B2 | 8/2009 | Saadat et al. | |
| 7,703,459 B2 | 4/2010 | Saadat et al. | |
| 2002/0065523 A1 | 5/2002 | McAlister et al. | |
| 2002/0183768 A1 | 12/2002 | Deem et al. | |
| 2003/0065359 A1 * | 4/2003 | Weller et al. | 606/213 |
| 2004/0006351 A1 | 1/2004 | Gannoe et al. | |
| 2004/0162568 A1 * | 8/2004 | Saadat et al. | 606/139 |
| 2004/0225305 A1 | 11/2004 | Ewers et al. | |
| 2005/0055038 A1 * | 3/2005 | Kelleher et al. | 606/151 |
| 2005/0251158 A1 | 11/2005 | Saadat et al. | |
| 2005/0251165 A1 | 11/2005 | Vaughan et al. | |
| 2006/0106288 A1 | 5/2006 | Roth et al. | |
| 2006/0212048 A1 | 9/2006 | Crainich | |
| 2006/0253127 A1 * | 11/2006 | Bjerken | 606/139 |
| 2007/0032797 A1 * | 2/2007 | Ortiz et al. | 606/142 |
| 2007/0135803 A1 * | 6/2007 | Belson | 606/1 |
| 2007/0197864 A1 | 8/2007 | Dejima et al. | |
| 2007/0260114 A1 | 11/2007 | Miyamoto et al. | |

FOREIGN PATENT DOCUMENTS

| | | |
|---|---|---|
| CN | 1907241 A | 2/2007 |
| CN | 101325915 A | 12/2008 |
| EP | 1518498 A1 | 3/2005 |
| JP | 2006061689 A | 3/2006 |
| WO | 02060328 A1 | 8/2002 |
| WO | 2005115255 A1 | 12/2005 |
| WO | 2006055804 A2 | 5/2006 |
| WO | 2006093975 A2 | 9/2006 |
| WO | 2006112849 A1 | 10/2006 |

OTHER PUBLICATIONS

Partial European Search Report dated Mar. 20, 2008 issued in corresponding Application No. / Patent No. 07025128.5-1265.
Japanese Office Action dated Sep. 8, 2009 issued in corresponding Application No. 2007-337983 together with an English language translation.
U.S. Non-Final Office Action dated Dec. 7, 2010 issued in related U.S. Appl. No. 11/965,243.
U.S. Final Office Action dated Jun. 20, 2011 issued in related U.S. Appl. No. 11/965,243.
Chinese Office Action dated Oct. 23, 2012 issued in corresponding Application No. 201110048791.1 together with an English language translation.
U.S. Non-Final Office Action dated May 7, 2013 issued in related U.S. Appl. No. 11/965,243.
Chinese Office Action dated Aug. 9, 2013 issued in corresponding Application No. 201110048791.1 together with an English language translation.
U.S. Final Office Action dated Nov. 4, 2013 issued in related U.S. Appl. No. 11/965,243.

* cited by examiner

METHOD FOR SUTURING A GASTRIC WALL

This application is a divisional application based on U.S. patent application Ser. No. 11/965,243, filed on Dec. 27, 2007, now abandoned, whose priority is claimed on U.S. Provisional Application No. 60/877,517, filed Dec. 28, 2006, and U.S. Provisional Application No. 60/898,309, filed Jan. 30, 2007, the contents of each of which are incorporated herein by reference.

BACKGROUND OF THE INVENTION

1. Field of the Invention

The present invention relates to a natural orifice and gastric therapy system and relates to a method for suturing a gastric wall.

2. Background Art

In some therapeutic operations, a part of a stomach is cerclaged for the purpose of preventing obesity, etc. Peroral therapeutic operations are conducted while observing inside of a stomach by an endoscope passed through an overtube inserted from a mouth of a patient (see, for example, U.S. Pat. No. 7,083,629, U.S. Publication No. 2005/0251158, WO2006/055804, and WO2006/112849). These therapeutic operations use a cerclage therapeutic instrument passed through a job channel of the endoscope, e.g., an anterior wall and a posterior gastric wall are cerclaged to form a sleeve in the stomach.

However, in the above therapeutic operations, the gastric wall is a sack constituting two tissues, i.e., linking at a anterior wall and at a posterior wall. The linking point is difficult to be identified in the above therapeutic operations, since an endoscopic observation of inside the stomach provides a continuous view of the gastric wall. Therefore, a surgeon who conducts such an peroral therapeutic operation is required for considerable skill.

The present invention was conceived in view of the aforementioned circumstances, and an object thereof is to provide a gastric therapy system and a method for suturing a gastric wall that can allow a smooth and accurate gastric therapy operation for cerclaging a part of a stomach.

SUMMARY OF THE INVENTION

A first aspect of a gastric therapy system according to the present invention includes: a loop-forming member that forms a loop along a lesser-curvature-line and a greater-curvature-line in a stomach; a guide member that introduces the loop-forming member into the stomach; and a therapy section that cerclages a part of the gastric wall after looping the loop-forming member.

In the first aspect of the therapy system according to the present invention, the loop-forming member may be an insertion section of an endoscope; the guide member may be included in an overtube; and the therapy section may be attached to the insertion section.

In the first aspect of the therapy system according to the present invention, the loop-forming member and the guide member may be included in an overtube; and the therapy section may be attached to the distal end of the overtube.

In the first aspect of the gastric therapy system according to the present invention, the guide member may be included in an overtube, and the loop-forming member having elasticity may be an elongated rod capable of being inserted through the overtube.

In the first aspect of the therapy system according to the present invention, the loop-forming member may be elastic and may be elongate; and the therapy section may be attached to the distal end of the loop-forming member.

In the first aspect of the gastric therapy system according to the present invention, the therapy section may be a cerclage instrument that comprises: a cylindrical main unit; a pair of holes, formed on the main unit, that are capable of retracting the gastric wall; a tissue-dissecting instrument for dissecting a mucosa of the gastric wall that is retracted into the main unit from the pair of holes; and a tissue-cerclage instrument for cerclaging two-dissected gastric walls in which the mucosa have been dissected.

In the first aspect of the gastric therapy system according to the present invention, the therapy section may further include a pair of first gastric-wall-fixing sections for fixing the two gastric walls that are retracted into the main unit from the pair of holes; and a pair of second gastric-wall-fixing sections for fixing the two gastric walls in which the mucosa have been dissected by the tissue-dissecting instrument. In addition, the tissue-dissecting instrument may dissect the mucosa of the gastric walls each fixed to the pair of first gastric-wall-fixing sections, and the tissue-cerclage instrument may cerclage the gastric wall fixed to one of the second gastric-wall-fixing sections to the gastric wall fixed to the other one of the second gastric-wall-fixing section.

The first aspect of the gastric therapy system according to the present invention may further include a link apparatus for connecting the therapy section to the loop-forming member or the guide member when the loop-forming member forms a loop in the stomach.

A second aspect of the gastric therapy system according to the present invention includes an arc member, wherein the arc member is inserted into a stomach perorally; the arc member is disposed along a lesser-curvature-line and a greater-curvature-line in the stomach, and the arc member imparts a substantial uniform tension to an anterior wall and a posterior gastric wall.

A cerclage instrument according to the present invention being inserted into a stomach perorally for cerclaging a gastric wall in the stomach includes: a cylindrical main unit; a pair of holes formed on the main unit that are capable of retracting the gastric wall; a tissue-dissecting instrument for dissecting a mucosa of the gastric wall retracted into the main unit from the pair of holes; and a tissue-cerclage instrument for cerclaging the two gastric walls in which the mucosa have been dissected.

The cerclage instrument according to the present invention may further include: a pair of first gastric-wall-fixing sections for fixing the two gastric walls that are retracted into the main unit from the pair of holes; and a pair of second gastric-wall-fixing sections for fixing the two gastric walls in which the mucosa have been dissected by the tissue-dissecting instrument. In addition, the tissue-dissecting instrument may dissect the mucosa of the gastric walls each fixed to the pair of first gastric-wall-fixing sections, and the tissue-cerclage instrument may cerclage the gastric wall fixed to one of the second gastric-wall-fixing sections to the gastric wall fixed to the other one of the second gastric-wall-fixing section.

In the cerclage instrument according to the present invention, the first gastric-wall-fixing section may be disposed innermore in the main unit relative to the position of the tissue-dissecting instrument by the thickness of the mucosa of the gastric wall retracted into the main unit.

In the cerclage instrument according to the present invention, the tissue-dissecting instrument may be a wire for dissecting the mucosa of the gastric wall by supplying high-frequency electricity.

In the cerclage instrument according to the present invention, the tissue-cerclage instrument may be one of a fastener, a stapler, a clip, a tag, a T-bar, and a clamp.

In the cerclage instrument according to the present invention, the tissue-cerclage instrument may further include: a needle that alternately punctures a muscle coat of the gastric wall retracted into the main unit from one of the holes and a muscle coat of the gastric wall retracted into the main unit from the other one of the holes and passes a suture thread through the muscle coats; and a thread-releasing member for removing the needle while disposing the suture thread in the muscle coat.

In the cerclage instrument according to the present invention, an interval between a puncture position of the needle and the position of the second gastric-wall-fixing section may be smaller than the thickness of the muscle coat of the gastric wall so that the needle can puncture the muscle coat of the gastric wall retracted into the main unit.

In the cerclage instrument according to the present invention, the needle may have a spiral shape so that the needle can alternately puncture the muscle coat of the gastric wall retracted into the main unit from one of the holes and the muscle coat of the gastric wall retracted into the main unit from the other one of the holes.

In the cerclage instrument according to the present invention, the needle may be bent so that the needle can alternately puncture the muscle coat of the gastric wall retracted into the main unit from one of the holes and the muscle coat of the gastric wall retracted into the main unit from the other one of the holes.

In the cerclage instrument according to the present invention, the main unit may include: an outer cylinder section having the holes formed thereon; and an inner cylinder section having the first gastric-wall-fixing section and the second gastric-wall-fixing section, the inner cylinder section being capable of housing the mucosa dissected from the gastric wall, and the inner cylinder section being capable of rotating, or advancing and retracting.

A method for cerclaging a gastric wall includes: inserting an elastic long length of loop-forming member perorally into the stomach and advancing the loop-forming member along a lesser-curvature-line; returning the loop-forming member at the vicinity of a pyloric antrum of the stomach, advancing loop-forming member along a greater-curvature-line; forming a loop in the stomach; suctioning air from the stomach after looping the loop-forming member in the stomach, and shrinking the stomach so that an anterior gastric wall is in proximity with a posterior gastric wall within the looped loop-forming member; and cerclaging the anterior gastric wall and the posterior gastric wall that are in proximity by shrinking the stomach.

In the method for cerclaging the gastric wall according to the present invention, a suture thread may be punctured through the anterior wall and the posterior wall alternately while rotating a bent needle when the anterior gastric wall and the posterior gastric wall are cerclaged.

The method for cerclaging the gastric wall according to the present invention may include dissecting mucosa of tissues that should be adhered after the cerclage before cerclaging the anterior gastric wall and the posterior gastric wall.

The method for cerclaging the gastric wall according to the present invention may include embedding an implant into the gastric wall after cerclaging the anterior gastric wall and the posterior gastric wall.

In the method for cerclaging the gastric wall according to the present invention, a position for embedding the endoscope may be an entrance in the vicinity of a cardia of the stomach of a section that is cerclaged; an exit in the vicinity of the pylorus of the stomach; or a whole length or a part of the section that is cerclaged.

In the method for cerclaging the gastric wall according to the present invention, the implant may be a metal or resin coil, or a suture thread.

The method for cerclaging the gastric wall according to the present invention may further include: measuring thicknesses of a mucosa and a muscle coat of the gastric wall that should be cerclaged before or after inserting a cerclage instrument that cerclages the anterior gastric wall and the posterior gastric wall; selecting the cerclage instrument suitable for the measured thicknesses of the mucosa and the muscle coat, and cerclaging the mucosa of the gastric wall by using the cerclage instrument.

In the method for cerclaging the gastric wall according to the present invention, the thicknesses of the mucosa and the muscle coat of the gastric wall may be measured by using an ultrasonic endoscope or an ultrasonic searcher attached to the cerclage instrument.

The method for cerclaging the gastric wall according to the present invention may further include: measuring thicknesses of a mucosa and a muscle coat of the gastric wall that should be cerclaged before or after inserting a cerclage instrument that cerclages the anterior gastric wall and the posterior gastric wall; selecting the cerclage instrument suitable for the measured thicknesses of the mucosa and the muscle coat, and cerclaging the mucosa of the gastric wall by using the cerclage instrument.

In the method for cerclaging the gastric wall according to the present invention, the thicknesses of the mucosa and the muscle coat of the gastric wall may be measured by using an ultrasonic endoscope or an ultrasonic searcher attached to the cerclage instrument.

A method for cerclaging a gastric wall includes: inserting a flexible elongated loop-forming member perorally into the stomach and advancing the loop-forming member along a lesser-curvature-line; returning the loop-forming member at a position closer to an oral side than a pyloric antrum of the stomach, advancing loop-forming member along a greater-curvature-line; forming a loop in the stomach; suctioning air from the stomach after looping the loop-forming member in the stomach, and shrinking the stomach so that an anterior gastric wall is in proximity with a posterior gastric wall within the looped loop-forming member; and cerclaging the anterior gastric wall and the posterior gastric wall that are in proximity by shrinking the stomach.

In the method for cerclaging the gastric wall according to the present invention, a position for embedding the implant may be an entrance in the vicinity of a cardia of the stomach of a section that is cerclaged; an exit in the vicinity of the pylorus of the stomach; or a whole length or a part of the section that is cerclaged.

According to the gastric therapy system and the method of the present invention for cerclaging the gastric wall, therapeutic operations for cerclaging a part of the stomach can be conducted smoothly and accurately irrespective of the skill of a surgeon.

BRIEF DESCRIPTION OF DRAWINGS

FIG. 4 is a schematic view illustrating the endoscope that is advanced upon disposing the overtube at a predetermined position, and an insertion section of the endoscope looped in the stomach in the first embodiment of the present invention wherein.

PREFERRED EMBODIMENTS

First Embodiment

Figure 1:
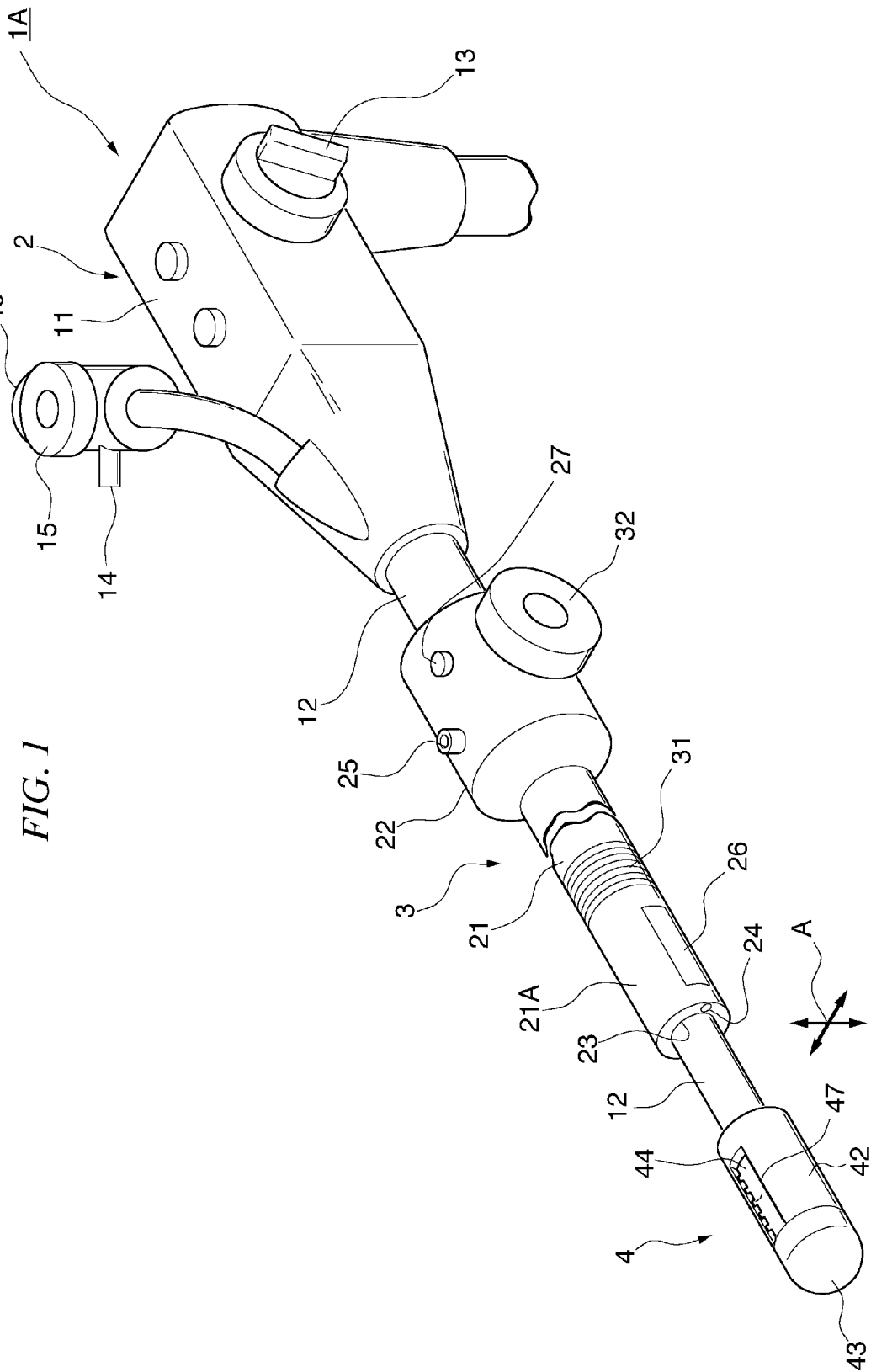
FIG. 1 shows a first embodiment of the present invention where a cerclage instrument is attached to a distal end of an endoscope that is passed through an overtube.

As illustrated in FIG. 1, a therapy system 1A according to the present embodiment has an endoscope 2; an overtube 3 passed through the endoscope 2; and a cerclage instrument 4 which serves as a therapy section for cerclaging a part of a gastric wall.

The endoscope 2 has a maneuvering section 11 that is maneuvered by a surgeon; and a long length of elastic insertion section 12. The insertion section 12 extending from the maneuvering section 11 serves as a loop-forming member that forms a loop in a stomach ST. Disposed at the punching instrument of the insertion section 12 are an observation device and a lighting device that are not shown in the drawing. A lumen undertaking air-suction, water-supply, or allowing an instrument like forceps to pass therethrough is formed from the distal end of the insertion section 12 to the maneuvering section 11 in the insertion section 12. Manipulating a knob 13 disposed on the maneuvering section 11 allows the distal end of the insertion section 12 to bend in two directions indicated by an arrow A in the drawing.

The overtube 3 has an elastic cylindrical main unit 21; and a manipulation section 22 that is manipulated by the surgeon. The main unit 21 extending from the manipulation section 22 serves as a guide member that introduces the insertion section 12 into the stomach ST. An opening section 23 that permits the endoscope 2 to pass therethrough is formed on the distal end of the main unit 21. Provided in the opening section 23 is a seal member, not shown in the drawing, that assures the air-tightness between the insertion section 12 and the overtube 3 when the insertion section 12 is passed through the opening section 23. A suction lumen 24 is formed in the overtube 3. An end of the suction lumen 24 opens at the distal end of the main unit 21, and the other end of the suction lumen 24 communicates with a suction mouthpiece 25 provided on a lateral section of the manipulation section 22.

A Solenoid 26 serving as a link apparatus of the overtube 3 is attached onto a lateral surface of the distal end section 21A of the main unit 21. The Solenoid 26 is elongated along the axial line of the main unit 21. Switching, i.e., turning on or turning off a Solenoid switch 27 disposed at the side of the manipulation section 22 permits electricity to be supplied to the Solenoid 26 from a power supply that is not shown in the drawing. Preferably, the Solenoid 26 should be disposed on a left-hand side viewed in a direction toward the distal end from the proximal end of the overtube 3 when the overtube 3 is disposed so that the Solenoid switch 27 is directed upward. The disposition of the Solenoid 26, however, may not be limited to this configuration. It should be noted that the link apparatus of the overtube 3 may be replaced by a permanent magnet instead of the Solenoid 26. Since this case of the manipulation section 22 does not need a switch, the configuration of the device can be simplified. Preferably, the permanent magnet should be disposed similarly to the Solenoid 26.

A corrugated bending section 31 is disposed on a part of the overtube 3 proximal relative to the Solenoid 26. The bending section 31 is formed by assembling corrugated tubes, etc. Manipulating a bending handle 32 of the manipulation section 22 allows the overtube 3 to be bent around the bending section 31.

Figure 2:
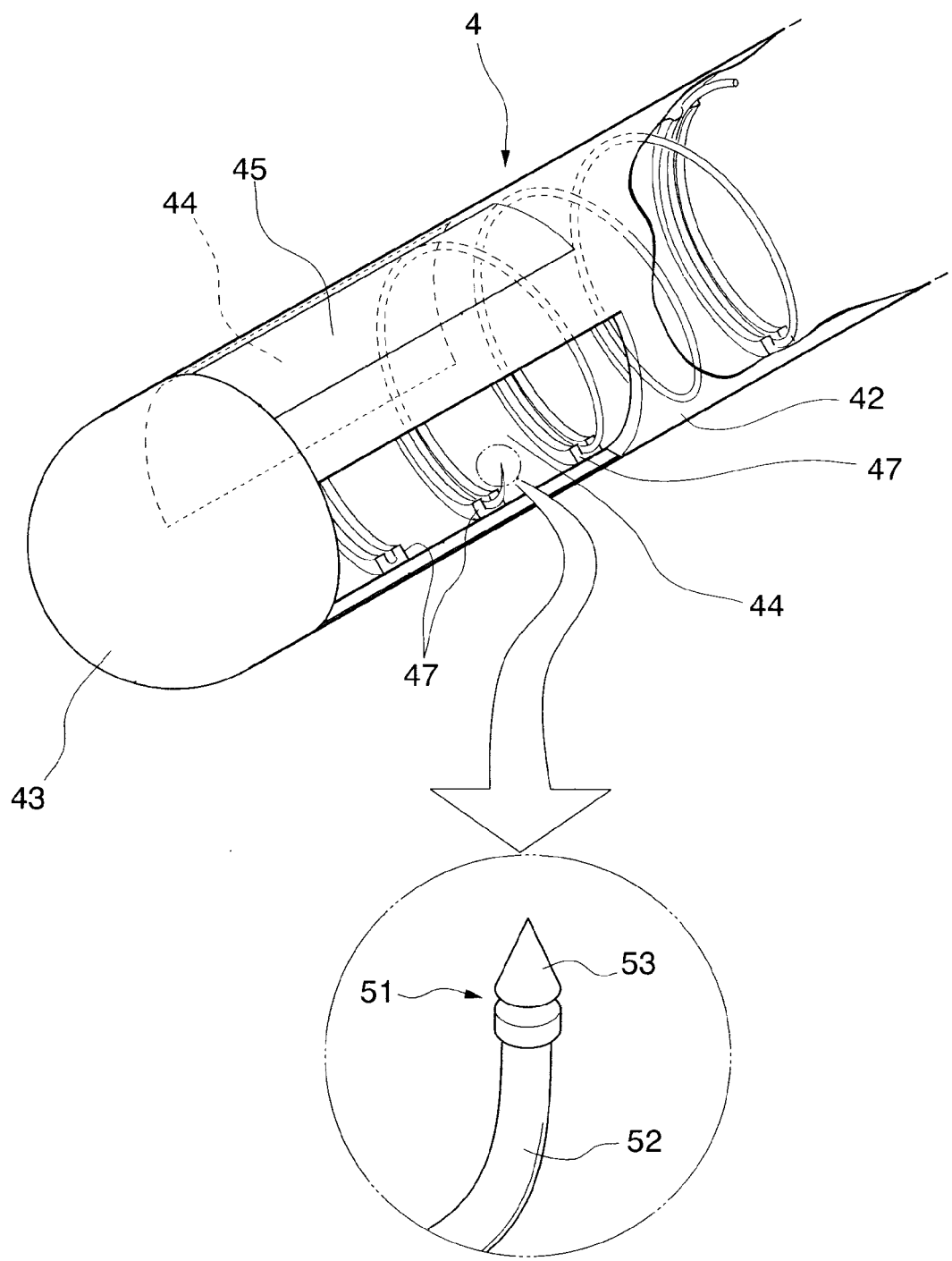
FIG. 2 is a perspective view of the cerclage instrument according to the first embodiment of the present invention.

A cerclage instrument 4, detachably attached to the distal end of the insertion section 12, has a cylindrical main unit 42; and a transparent distal end cap 43 that covers the distal end of the main unit 42. The size and transparency of the distal end cap 43 are significant for obtaining perspective of the observation device in the endoscope 2. As illustrated in FIGS. 1 and 2, two side holes 44 serving as therapeutic windows are formed on peripheries of the main unit 42. The side holes 44 are disposed one by one symmetrically with respect to the central axis of the main unit 42. Each side hole 44 is elongated in the central axis direction of the main unit 42. A permanent magnet 45 that serves as a link apparatus of the cerclage instrument 4 is attached to a portion of the main unit 42 where the side holes 44 are not formed. Preferably, the permanent magnet 45 should be disposed on a right-hand side viewed in the direction toward the distal end from the proximal end of the overtube 3 when the overtube 3 is disposed so that the Solenoid switch 27 is directed upward. In other words, the permanent magnet 45 having a side hole 44 directed upwardly and the other side hole 44 directed downwardly is disposed opposite the Solenoid 26 of the overtube 3. It should be noted that the link apparatus of the cerclage instrument 4 may be made from a magnetic member such as metal instead of the permanent magnet 45.

As illustrated in FIG. 2, a spiral groove 47 is formed on an inner periphery of the main unit 42. A spiral needle 51 serving as a tissue-cerclage instrument is passed through the groove 47. The spiral needle 51 is constituted by a hollow and spirally-formed bending-needle section 52 consistent with the groove 47; and a needle distal end section 53 having an acute distal end. The needle distal end section 53 is detachably attached to the distal end of the bending-needle section 52. A suture thread, not shown in the drawing, is fixed, e.g., crimped onto the needle distal end section 53. The suture thread is passed through the bending-needle section 52. The spiral needle 51 is connected to a rod, not shown in the drawing, that is passed through the lumen of the insertion section 12 in the endoscope 2. The rod is joined to a manipulation handle 15 disposed on the manipulation section 11 of the endoscope 2. Rotating the manipulation handle 15 allows advancement and retraction of the rod. Advancing the rod causes the spiral needle 51 to advance while rotating in the spiral direction along the groove 47.

A manipulation section 40 extending toward the manipulation section 11 through the lumen of the insertion section 12 of the endoscope 2 undertakes manipulation of the cerclage instrument 4. As illustrated in FIG. 1, the manipulation section 40 is provided with a mouthpiece 14 of the suction lumen; and a manipulation handle 15 that rotates the spiral needle 51. It should be noted that the formation of the manipulation handle 15 is not limited to that shown in the drawing.

Therapeutic operation in the present embodiment is explained.

The insertion section 12 of the endoscope 2 is first inserted through the overtube 3, and the cerclage instrument 4 is attached to the distal end of the insertion section 12 projecting from the distal end of the overtube 3. The cerclage instrument 4 is attached to the distal end of the insertion section 12 so that the permanent magnet 45 is disposed on a right-hand side viewed in the direction toward the distal end from the proximal end of the overtube; one of the side holes 44 is disposed upward; and the other one of the side holes 44 is disposed downwardly, when the overtube 3 is disposed so that the Solenoid switch 27 is directed upward.

Figure 3:
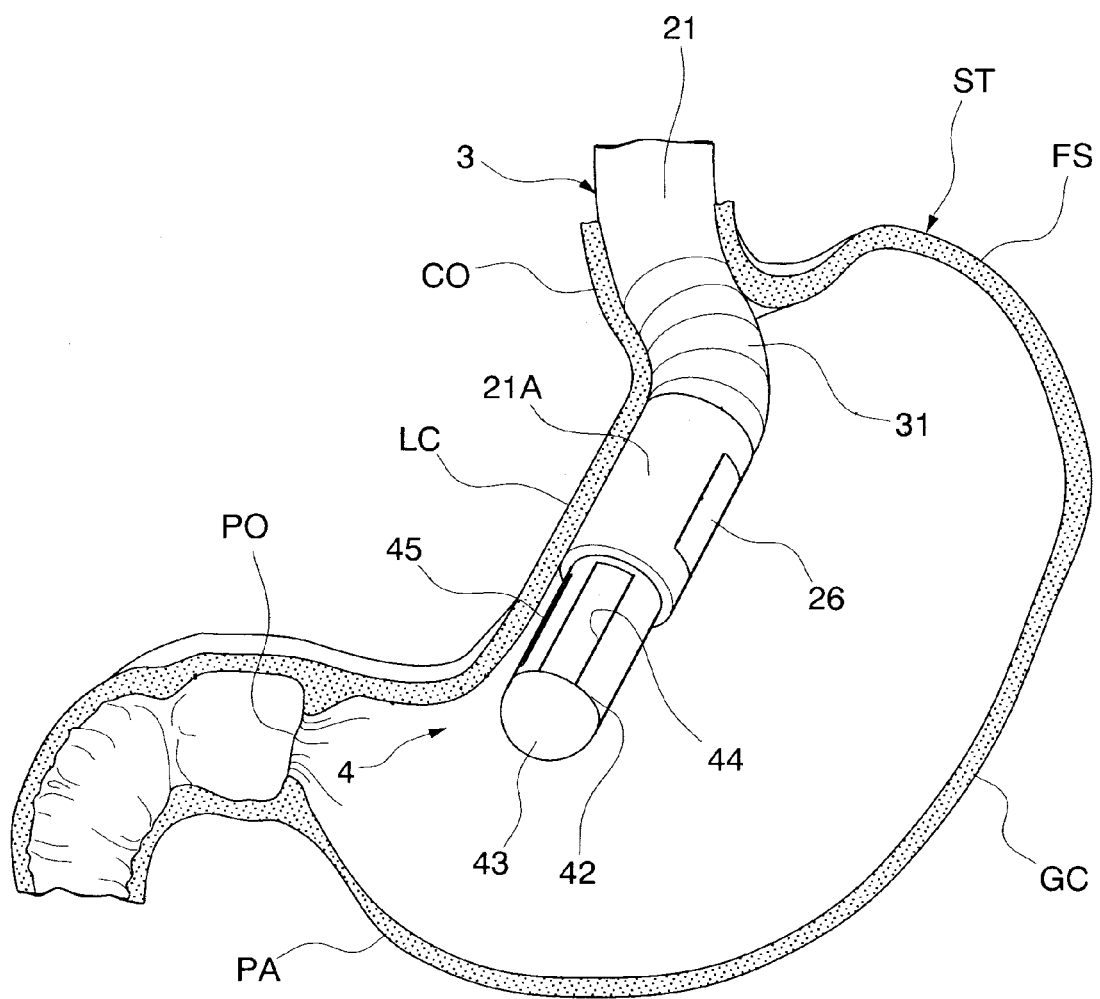
FIG. 3 is a schematic view of the distal end of the overtube according to the first embodiment of the present invention, inserted into a stomach.

As illustrated in FIG. 3, the insertion section 12 is retracted until the cerclage instrument 4 makes contact with the distal end of the overtube 3, and then, the overtube 3 is inserted into the stomach ST from the mouth of the patient. The overtube 3 is paused when a predetermined portion of the distal end section 21A of the main unit 21 of the overtube 3 enters the stomach. Consequently, the insertion of the overtube 3 is adjusted so that the bending section 31 reaches to the vicinity of a cardia CO; and so that the distal end section 21A is about to project into the stomach ST. Insertion is further adjusted so that the Solenoid 26 is directed to the greater-curvature-line GC of stomach ST relative to the Solenoid switch 27 illustrated in FIG. 1. The distal end section 21A is disposed along the lesser-curvature-line LC when the inserted overtube 3 is disposed by manipulating the bending handle 32 of the manipulation section 22 while observing an image inside of a patient obtained through a distal end cap 43 of the cerclage instrument 4 by using an observation device of the endoscope 2.

Subsequently, the insertion section 12 of the endoscope 2 is pushed into the stomach ST while the overtube 3 is paused. The insertion section 12 maintaining air-tightness between the insertion section 12 and the overtube 3 enters the stomach ST.

The insertion section 12 and the cerclage instrument 4 advance along the lesser-curvature-line LC of stomach ST toward the pyloric antrum PA, and hit the gastric wall in the vicinity of the pyloric antrum PA. The insertion section 12 and the cerclage instrument 4 upon hitting the gastric wall return along the greater-curvature-line GC of the stomach ST and further travel. Advancements of the insertion section 12 and the cerclage instrument 4 may be assisted in an arbitrary direction by manipulating the knob 13 if necessary in this case.

Figure 4:
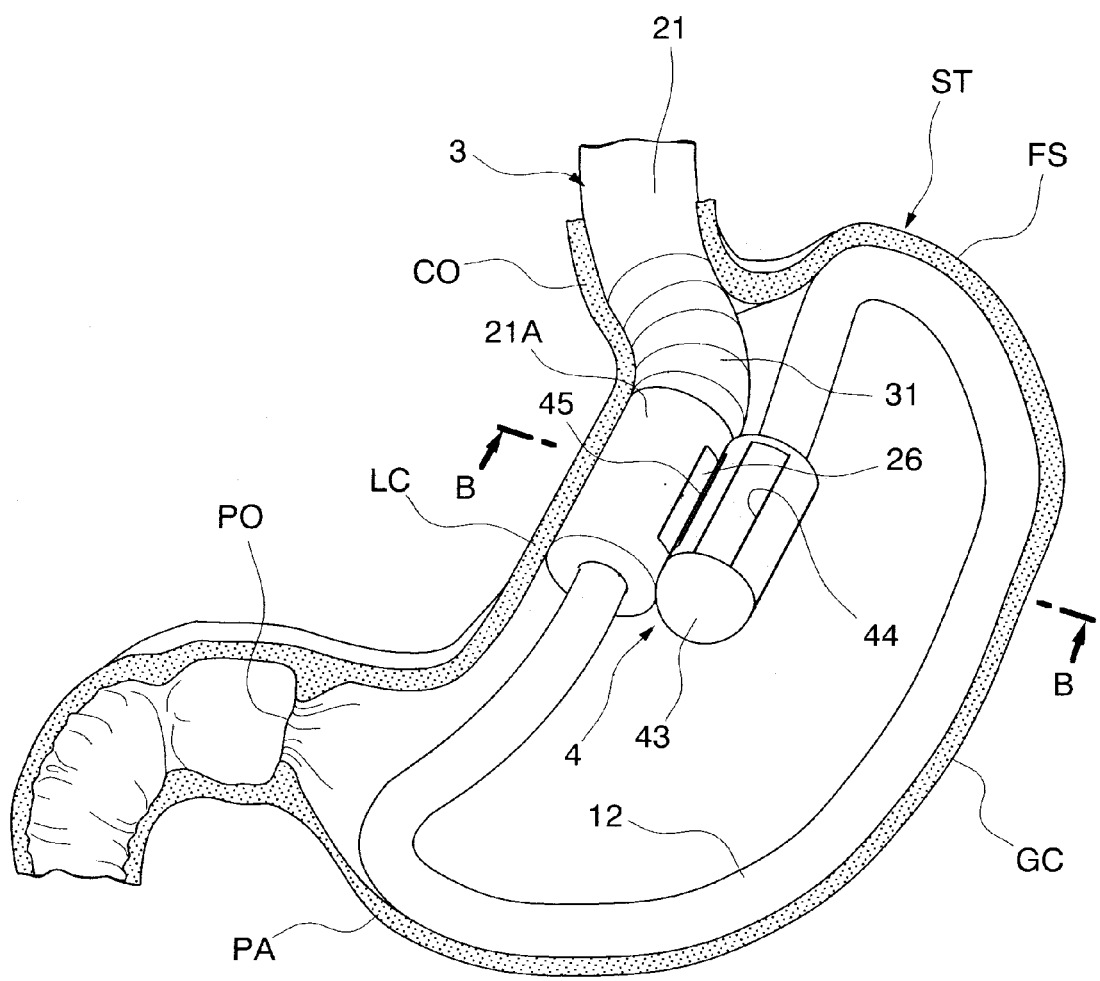

Accordingly, as illustrated in FIG. 4, the insertion section 12 and the cerclage instrument 4 project from the overtube 3 in the vicinity of the cardia CO; travel along the lesser-curvature-line LC, the greater-curvature-line GC, and the gastric fundus FS; and return to the vicinity of the distal end section 21A of the overtube 3. The insertion section 12 thus forms a loop. The cerclage instrument 4 upon returning to the vicinity of the distal end section 21A is disposed in proximity with the Solenoid 26. Turning on the Solenoid switch 27 causes electricity to flow in the Solenoid 26, thereby absorbing the permanent magnet 45. Accordingly, the overtube 3 joins with the cerclage instrument 4 via the Solenoid 26 and the permanent magnet 45. Meanwhile, in a case where the link apparatus of the overtube 3 uses a permanent magnet, the cerclage instrument 4 in proximity with the distal end section 21A is automatically absorbed. The permanent magnet 45 may be displaced by rotating the insertion section 12 around the axis if the permanent magnet 45 of the cerclage instrument 4 is offset relative to the permanent magnet of the overtube 3.

Figure 5:
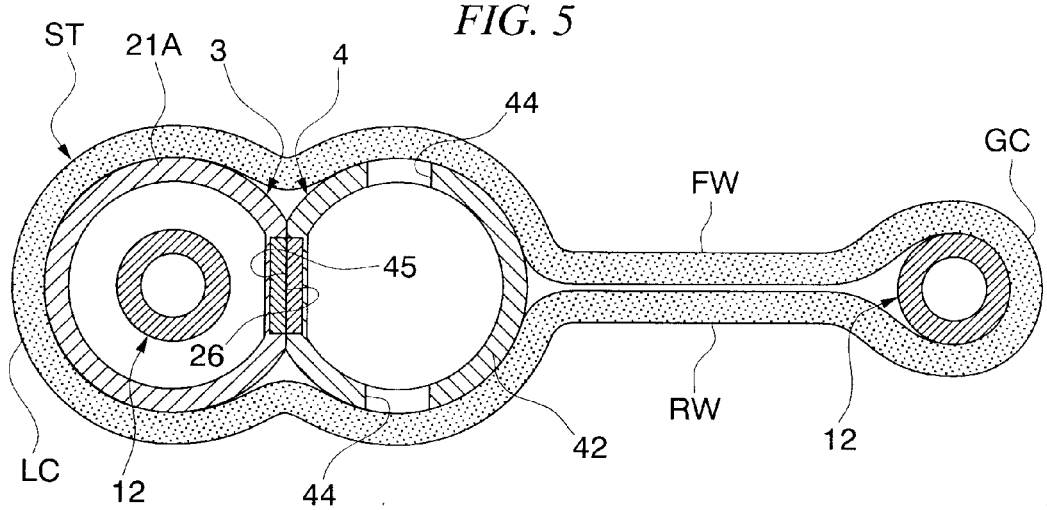
FIG. 5 is cross-section viewed along the B-B line of FIG. 4 according to the first embodiment of the present invention.

Air in the stomach ST is suctioned by a suction apparatus, not shown in the drawing, connected to a suction mouthpiece 25 of the overtube 3. The stomach ST shrinks while the gastric wall along the lesser-curvature-line LC and the gastric wall along the greater-curvature-line GC are seized by the overtube 3 and the insertion section 12 since the loop formed by the insertion section 12 is not reduced in size if the air in the stomach ST is suctioned. As illustrated in FIG. 5, the stomach ST shrinks in the looped insertion section 12 so that the anterior wall FW is in proximity with the posterior wall RW. The shrink of the stomach ST imparts a substantial uniform tension to the anterior wall FW and the posterior wall RW of the stomach ST defined by the looped part of the insertion section 12; thus, the anterior wall FW overlaps the posterior wall RW in close contact. That is, the insertion section 12 serves as an arc member. In a case where the patient is lying on his or her back, the anterior wall FW of the stomach ST is disposed on a looped portion of the insertion section 12; and the posterior wall RW is disposed under the looped portion. Attitude of the cerclage instrument 4 is stabilized since the cerclage instrument 4 is fixed to the distal end section 21A of the overtube 3 by the Solenoid 26; and since the gastric wall makes close contact with the periphery of the cerclage instrument 4.

A part of the gastric wall ST is cerclaged by using the cerclage instrument 4 upon stabilizing the attitude of the cerclage instrument 4.

Figure 6:
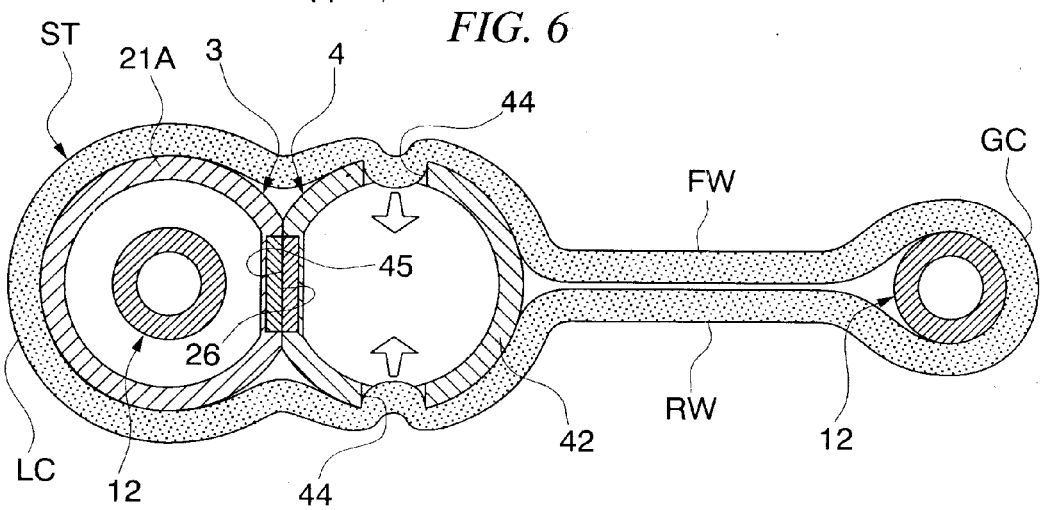
FIG. 6 is a cross-sectional view according to the first embodiment of the present invention, illustrating the anterior wall and the posterior gastric wall suctioned into a cerclage instrument.

The air in the cerclage instrument 4 is first suctioned through the suction lumen of the endoscope 2. Accordingly, the gastric walls are suctioned into the cerclage instrument 4 through the pair of side holes 44. The pair of side holes 44 of the main unit 42 are disposed vertically when the patient is lying on his or her back since the Solenoid 26 of the overtube 3 is directed to the greater-curvature-line GC; the insertion section 12 is looped; and then the permanent magnet 45 of the cerclage instrument 4 is suctioned by the Solenoid 26. That is, one of the side holes 44 faces the anterior wall FW of the stomach ST, and the other one of the side holes 44 faces the posterior wall RW of the stomach ST. Therefore, as illustrated in FIG. 6, suctioning the gastric wall through the side holes 44 of the main unit 42 causes the anterior wall FW to be retracted into the cerclage instrument 4 through the upper side hole 44 and the posterior wall RW to be retracted into the cerclage instrument 4 through the lower side hole 44.

Figure 7:
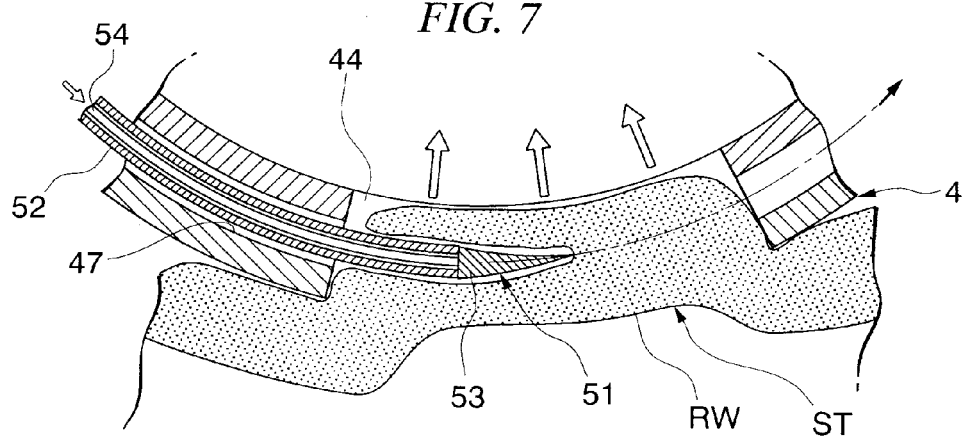
FIG. 7 illustrates how to puncture a needle into a muscle coat of the stomach in cross-sectional view according to the first embodiment of the present invention.

Manipulating the manipulation handle 15 of the endoscope 2 causes the spiral needle 51 to advance while rotating in the spiral direction along the groove 47. As illustrated in FIG. 7, the spiral needle 51 penetrates the wall (e.g., a muscle coat under a mucosa) of stomach retracted in the side hole 44 when the spiral needle 51 traverses the side hole 44. The spiral needle 51 upon advancing to the distal end of the groove 47 punctures the anterior wall FW and the posterior wall RW alternately. Manipulating the manipulation handle 15 in the reverse direction upon removing the needle distal end section 53 of the spiral needle 51 from the bending-needle section 52 causes only the bending-needle section 52 to retract while rotating in the spiral direction, thereby removing the bending-needle section 52 from the anterior wall FW and the posterior wall RW. The suture thread 54 remains in the stomach ST so that the suture thread 54 passes through the bending-needle section 52 and penetrates the anterior wall FW and the posterior wall RW alternately. For example, a forceps passing through the endoscope 2 for grasping the needle distal end section 53 may be used in a method for removing the needle distal end section 53 from the bending-needle section 52. Other methods may be used.

Figure 8:
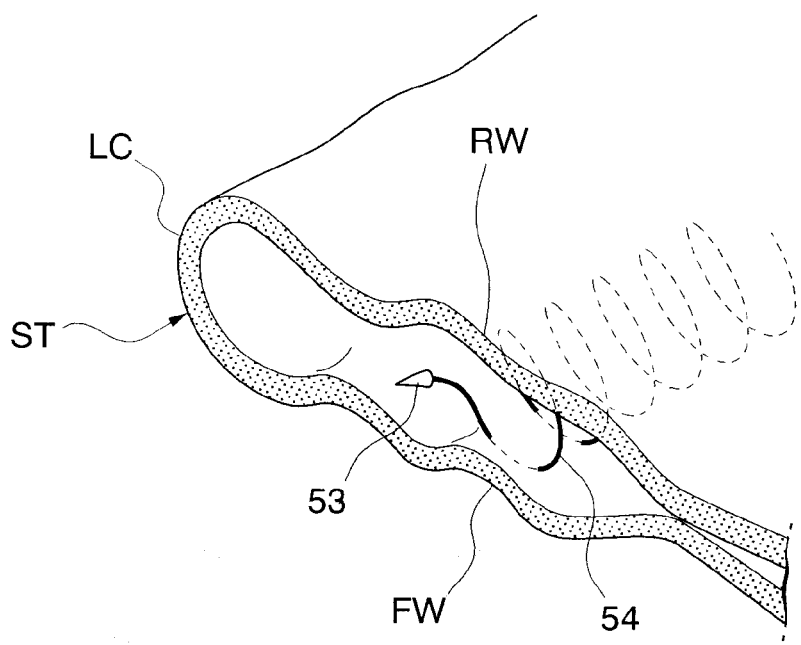
FIG. 8 is a schematic view of a removed state of the cerclage instrument upon passing a suture thread through the gastric wall.
Figure 9:
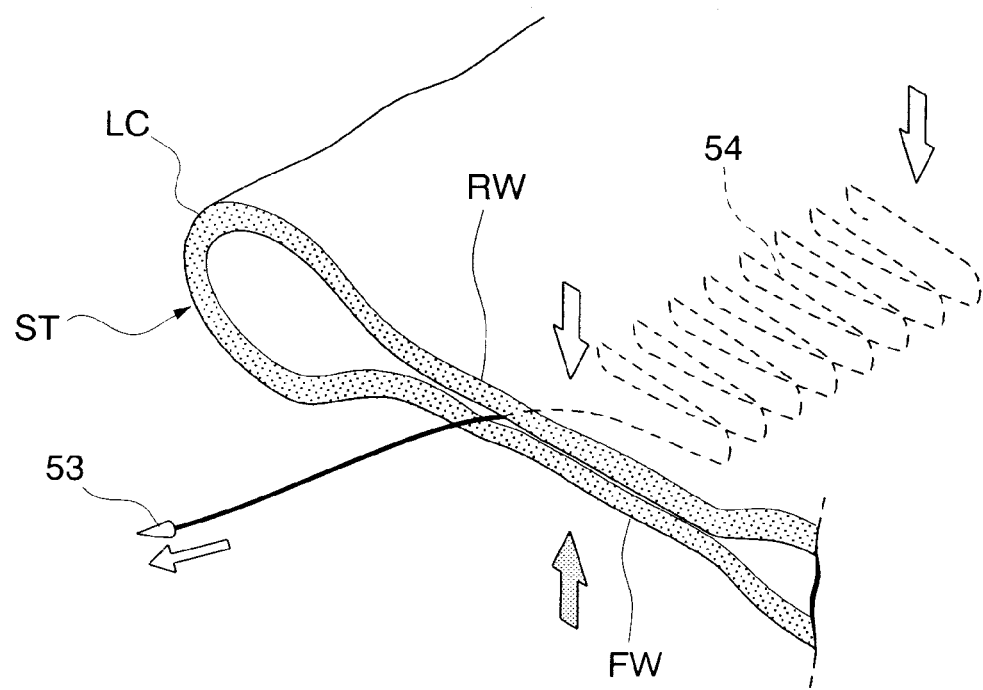
FIG. 9 is a schematic view illustrating a binded state of tissue by a suture thread according to the first embodiment of the present invention.

The suctioning of the air from the cerclage instrument 4 through the suction lumen of the endoscope 2 is paused. Consequently, the connection between the overtube 3 and the cerclage instrument 4 is released. The connection between these components can be released easily by turning off the Solenoid switch 27 if the Solenoid 26 is used. The connection between these components can be released by retracting the insertion section 12 if a permanent magnet is used. Pushing the distal end cap 43 by the endoscope 2 out of the main unit 42 and pulling apart the cerclage instrument 4 from the cerclaged part of the stomach ST cause the spirally-wound state of suture thread 54 to be indwelled in the stomach ST as illustrated in FIG. 8. Drawing the suture thread 54 by a forceps, etc., passing through the insertion section 12 and binding a tissue cause the anterior wall FW to contact closely with the posterior wall RW; and cause the closely-contacting part to be cerclaged as illustrated in FIG. 9. The insertion section 12 and the overtube 3 are removed from the inside of the body upon completing the treatments.

Figure 10:
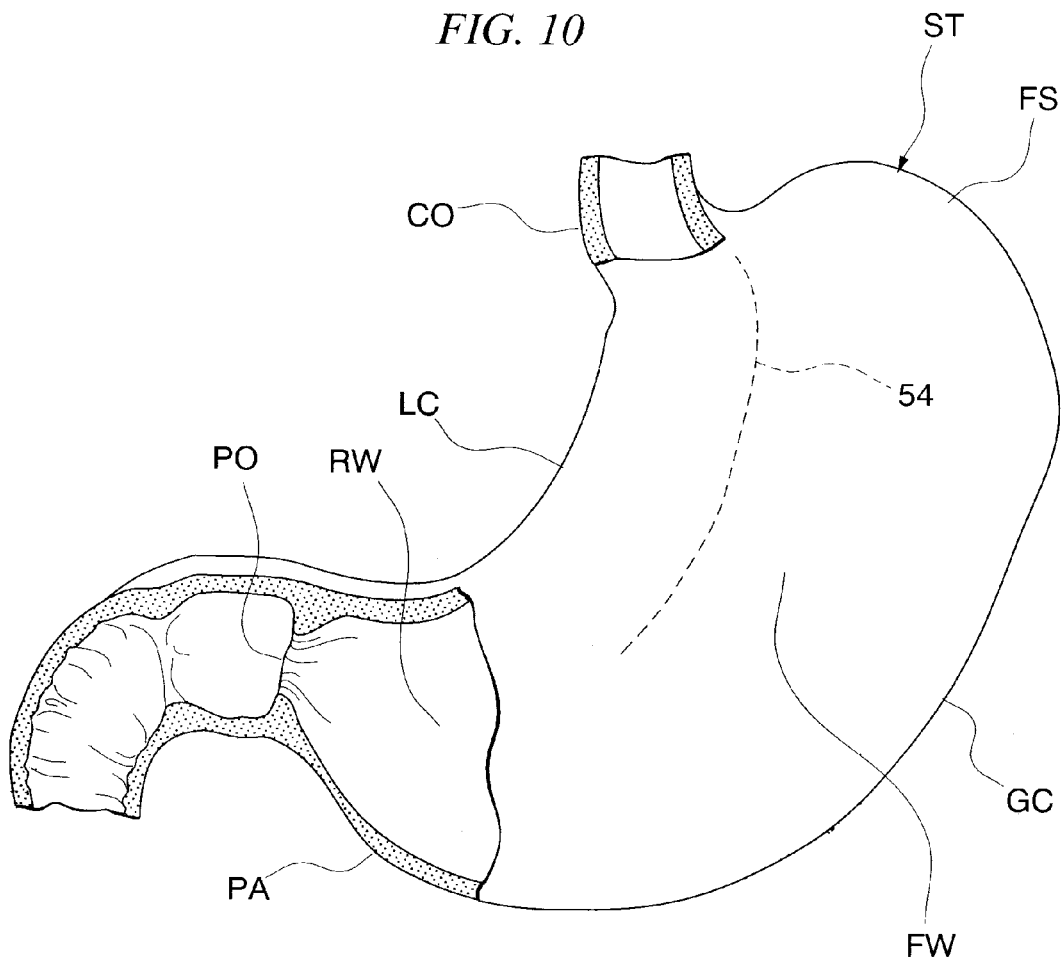
FIG. 10 is a schematic view according to the first embodiment of the present invention, illustrating an example of a sleeve formed in the stomach by binding the gastric wall.

The section cerclaged by the suture thread 54 forms a substantial cylindrical passway that extends from the cardia CO to the pylorus PO in the stomach ST as illustrated in FIG. 10. One can expect to prevent obesity since the constricted part of the stomach ST, specifically the vicinity of the cardia CO that undertakes incoming food, hinders the stomach ST from intaking a significant amount of food.

The present embodiment can shrink the stomach ST so that the anterior wall FW makes close contact with the posterior wall RW when the insertion section 12 of the endoscope 2 is pushed along the lesser-curvature-line LC and the greater-curvature-line GC into the stomach ST and then the air is suctioned from the stomach ST. Accordingly, the surgeon can acknowledge the accurate position to be cerclaged in the stomach ST; thereby facilitating the therapeutic operation.

The gastric wall can be cerclaged by retracting the anterior wall FW and the posterior wall RW of the stomach ST into the cerclage instrument 4; rotating the spiral needle 51; and using the suture thread 54 in the stomach ST. The therapeutic operation is easy, because procedures are simple and a complex apparatus is not necessary. An arbitrary position of the gastric wall can be cerclaged reliably since the overtube 3 is joined with the cerclage instrument 4 via the Solenoid 26 and the permanent magnet on this occasion; and the attitude of the cerclage instrument 4 is stabilized.

A diameter of the substantial cylindrical cerclaged passway can be the same as an outer diameter of the overtube 3 or greater than that. Therefore, a desirable size of passway can be formed when a narrow overtube 3 is used.

A modified example of the present embodiment is explained as follows.

Figure 11:
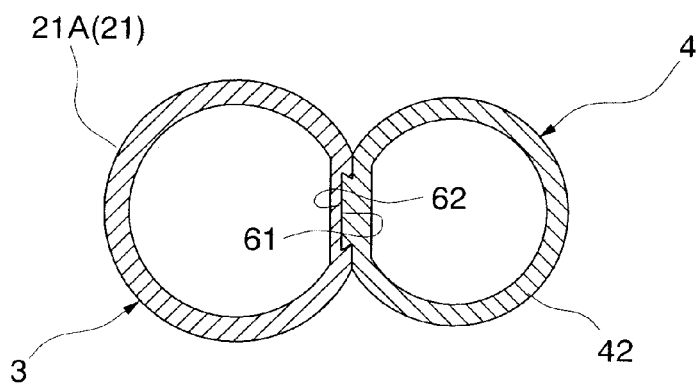
FIG. 11 is a cross-sectional view according to the first embodiment of the present invention, illustrating a modified example of a link apparatus that links the overtube to the cerclage instrument.

A link apparatus illustrated in FIG. 11 is constituted by a recessed section 61 formed on the distal end section 21A of the overtube 3; and a projecting section 62 formed on the cerclage instrument 4. The recessed section 61 can engage with the projecting section 62, that is, sliding of the overtube 3 or the cerclage instrument 4 in an axial direction of the overtube 3 allows them to be connected or separated easily. In addition, the recessed section 61 may be provided to the cerclage instrument 4, and the projecting section 62 may be provided to the overtube 3. It should be noted that the insertion of the overtube 3 into the body can be facilitated since the projecting section 62 does not interfere with an esophagus, etc. if the recessed section provided to the overtube 3.

Second Embodiment

Figure 12:
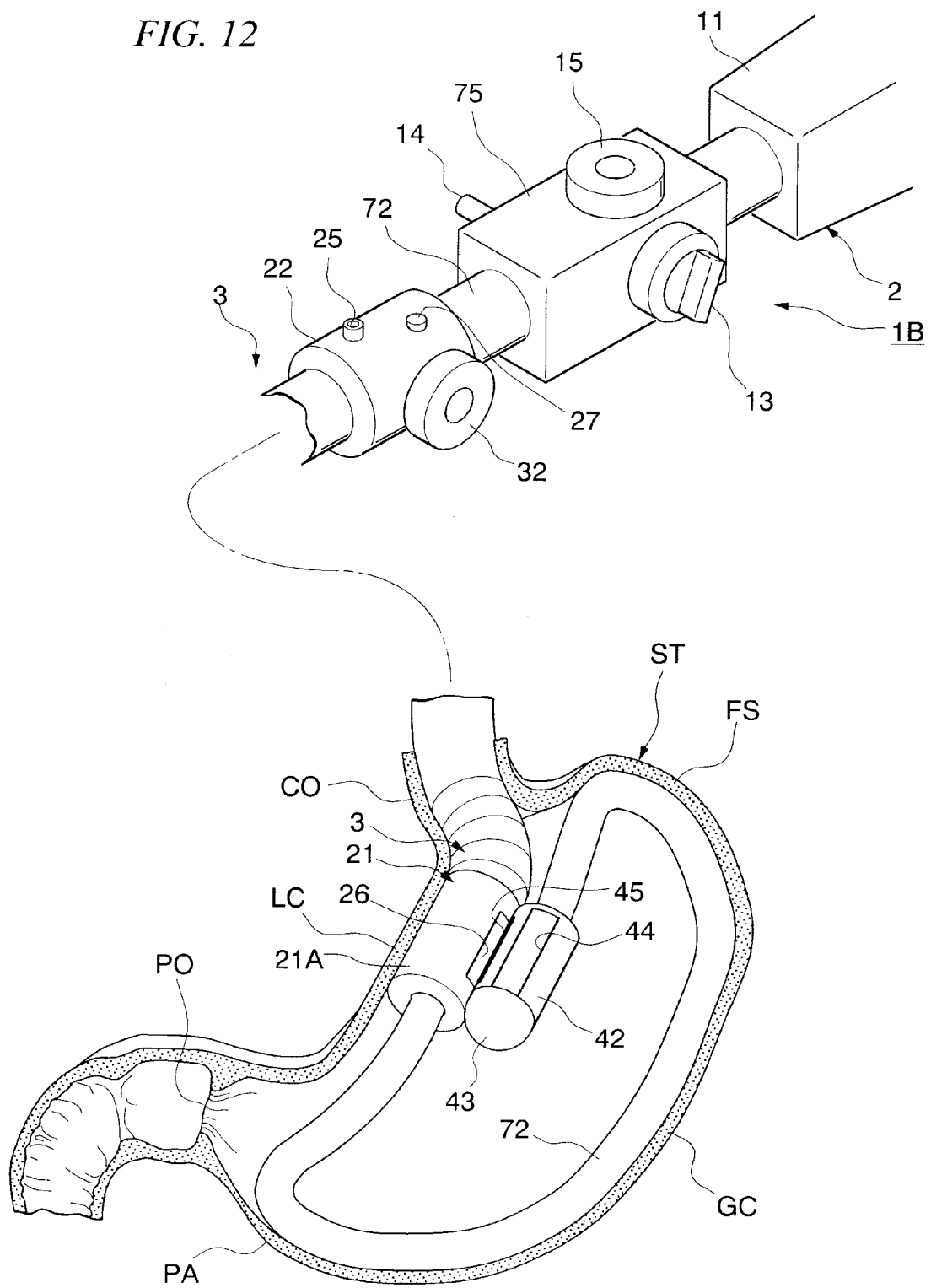
FIG. 12 is a schematic view of a cerclage instrument according to a second embodiment of the present invention having an insertion section looped in a stomach.
Figure 13:
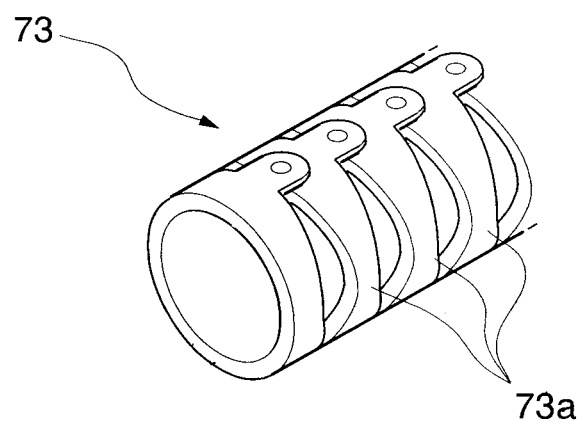
FIG. 13 is a perspective view according to the second embodiment of the present invention illustrating an example of a corrugated tube.
Figure 14:
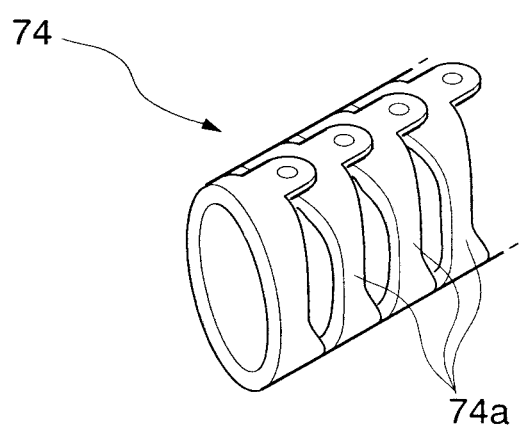
FIG. 14 is a perspective view according to the second embodiment of the present invention illustrating an example of the corrugated tube.

As illustrated in FIG. 12, a therapy system 1B in a second embodiment has an insertion section 72 that serves as a loop-forming member; and a cerclage instrument 4 that serves as a therapy section. The cerclage instrument 4 is detachably attached to the distal end of the insertion section 72. The insertion section 72 having elasticity extends from a manipulation section 75 of the cerclage instrument 4. In addition, the insertion section 72 is operative as a loop-forming member since the insertion section 72 passed through the overtube 3 has a length that enables to form a loop in the stomach ST. If necessary, the distal end of the insertion section 72 may be capable of bending. Specific configuration that enables the bending manipulation may be an insertion section 72 manufactured from a flexible material, or an assembly of corrugated tubes that is to be drawn by a wire. As illustrated in FIG. 13, each component 73a used in the corrugated tubes may have a cylindrical cross-section so that the insertion section 72 bends only along an arbitrary plane to form loop reliably. Also, as illustrated in FIG. 14, corrugated tubes 74 each having an elliptical cross-section may be employed to assure significant strength in a direction crossing to the bending direction. It should be noted that the cross-section of the corrugated tube is not limited to an ellipse, e.g., a deformed eclipse may be employed.

As illustrated in FIG. 12, the manipulation section 75 of the cerclage instrument 4 has a structure equivalent to that of the manipulation section 40 according to the first embodiment except a lumen that is capable of inserting an insertion section 12 of an endoscope 2 therethrough.

An observation device may be provided to the distal end of the cerclage instrument 4. Also, a channel that allows a forceps, etc., to be inserted therethrough may be formed in the insertion section 72. Furthermore, a lumen that allows the insertion section 12 of the endoscope 2 to be inserted therethrough may be formed in the insertion section 72.

Therapeutic operations equivalent to those of the first embodiment are conducted to cerclage a gastric wall. The insertion section 72 forms a loop instead of forming a loop by the insertion section 12 of the endoscope 2. Suctioning air in the stomach ST upon forming a loop imparts a substantial uniform tension to the anterior wall FW and the posterior wall RW of the stomach ST defined by the looped part of the insertion section 72; thus, the anterior wall FW overlaps the posterior wall RW in close contact. That is, the insertion section 72 serves as an arc member.

Third Embodiment

Figure 15:
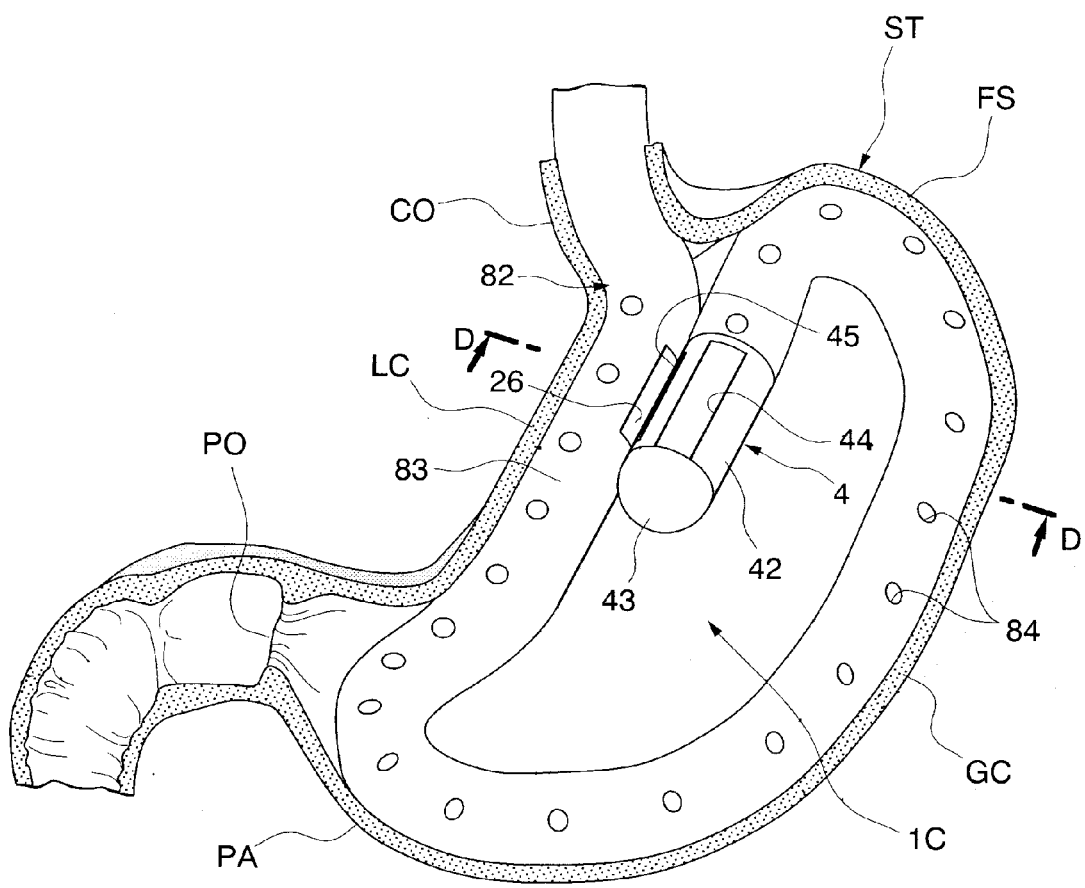
FIG. 15 is a schematic view of an overtube according to the second embodiment of the present invention having a cerclage instrument attached thereto looped in a stomach.

As illustrated in FIG. 15, a cerclage instrument 4 is attached to the distal end of an overtube 82 in a therapy system 1C according to a third embodiment. The overtube 82 has an elastic cylindrical main unit 83; and a manipulation section 22 (see FIG. 1) that is manipulated by the surgeon. The main unit 83 extending from the manipulation section 22 serves as a loop-forming member that forms a loop in a stomach ST. A Solenoid 26 serving as a link apparatus of the overtube 82 is attached onto a predetermined position of a lateral surface of the distal end section 21A of the main unit 83. In addition, a plurality of suction ports 84 are formed on a lateral surface of the main unit 83 with intervals along a longitudinal direction of the main unit 83. Air can be suctioned from the stomach ST through the suction ports 84. The main unit 83 may be produced by resin material or super elastic alloy, etc. Alternatively, the main unit 83 may be produced to have a corrugated tube construction that is capable of bending only in a predetermined direction so that a loop can be formed by the overtube 82 easily.

Figure 16:
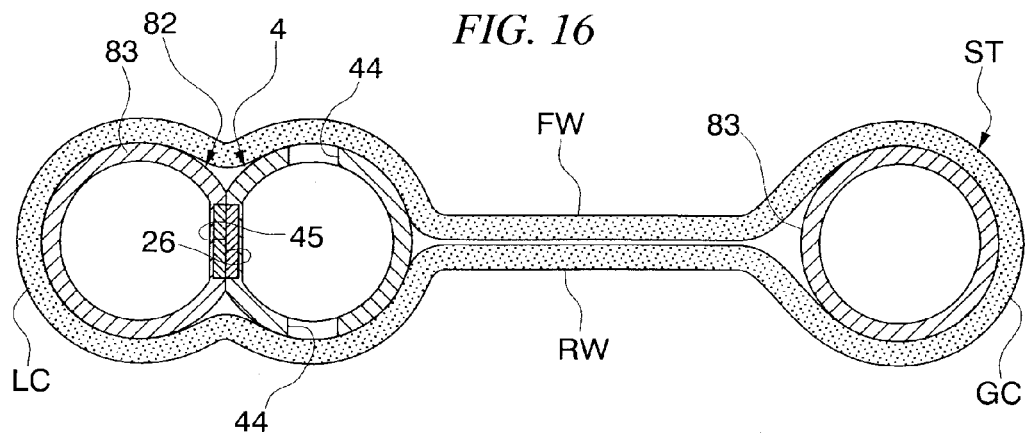
FIG. 16 is cross-section viewed along the D-D line of FIG. 15 according to a third embodiment of the present invention.

A loop used for a therapeutic operation is formed by introducing the main unit 83 of the overtube 82 to a pyloric antrum PA along a lesser-curvature-line LC; and further advancing the introduced main unit 83 to the vicinity of a cardia CO from the pyloric antrum PA along a greater-curvature-line GC. If necessary, the main unit 83 is bent to form a loop. Shrinking the stomach ST upon forming a loop by the main unit 83 imparts a substantial uniform tension to the anterior wall FW and the posterior wall RW of the stomach ST defined by the looped part of the main unit 83 of the overtube 82; thus, the anterior wall FW overlaps the posterior wall RW in close contact as illustrated in FIG. 16. That is, the main unit 83 serves as an arc member. The treatment for cerclaging the anterior wall FW and the posterior wall RW by the cerclage instrument 4 is the same as that previously explained.

The present embodiment irrespective of a simple configuration can obtain an effect equivalent to that of the above embodiments by attaching the cerclage instrument 4 to the distal end of the overtube 82. It is not necessary to insert a loop-forming instrument in addition to the overtube since the overtube 82 forms a loop. An image inside the stomach ST can be obtained through the transparent distal end cap 43 attached to the distal end of the cerclage instrument 4.

Figure 17:
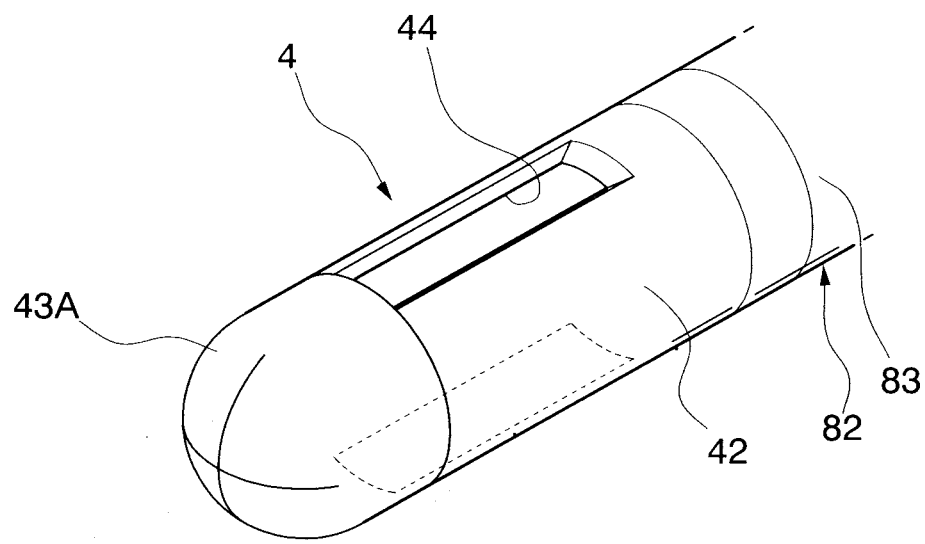
FIG. 17 is a perspective view illustrating a therapy section of the cerclage instrument according to the third embodiment of the present invention.
Figure 18:
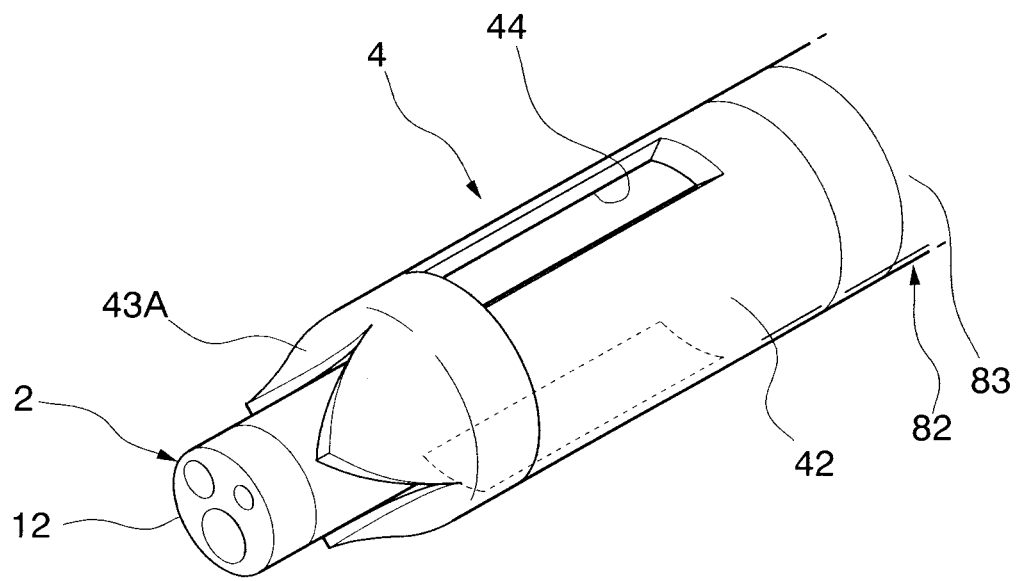
FIG. 18 is an endoscope according to the third embodiment of the present invention projecting from the distal end of the cerclage instrument.

As illustrated in FIGS. 17 and 18, a distal end cap 43A having an airtight valve may be attached to the distal end of the main unit 42 of the cerclage instrument 4. A cross slit is formed on the distal end cap 43A. The use of distal end cap 43A allows the insertion section 12 of the endoscope 2 to project from the distal end of the cerclage instrument 4 through the slit.

Figure 19:
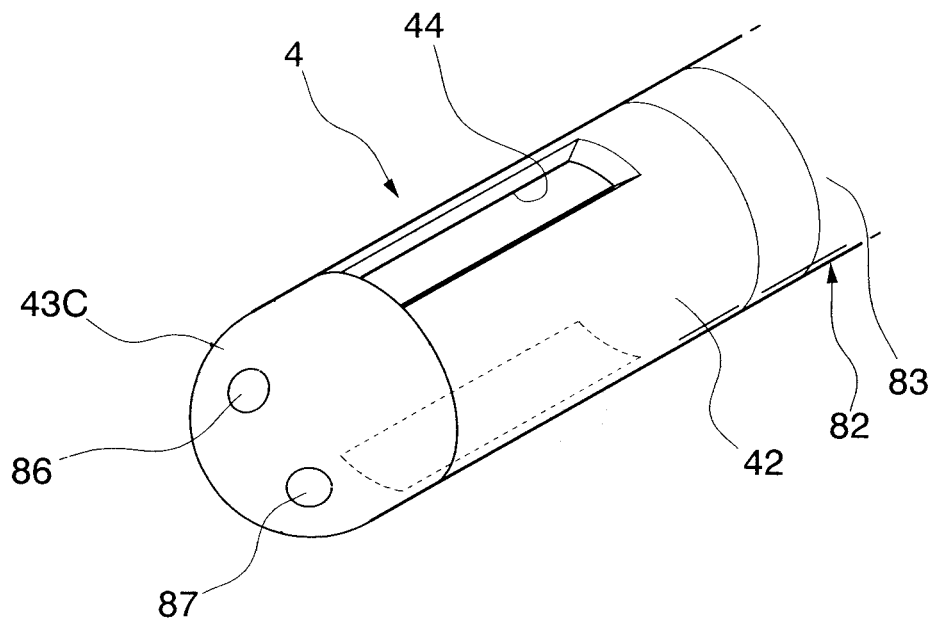
FIG. 19 is a perspective view illustrating a modified example of an observation device and a light-guide provided at the distal end of the cerclage instrument according to the third embodiment of the present invention.

As illustrated in FIG. 19, a distal end cap 43C having an observation device 86 and a light-guide 87 may be attached to the distal end of the main unit 42 of the cerclage instrument 4. Advancing or retracting manipulation of the cerclage instrument 4 or the overtube 82 can be conducted while observing the image obtained by the observation device 86.

Figure 20:
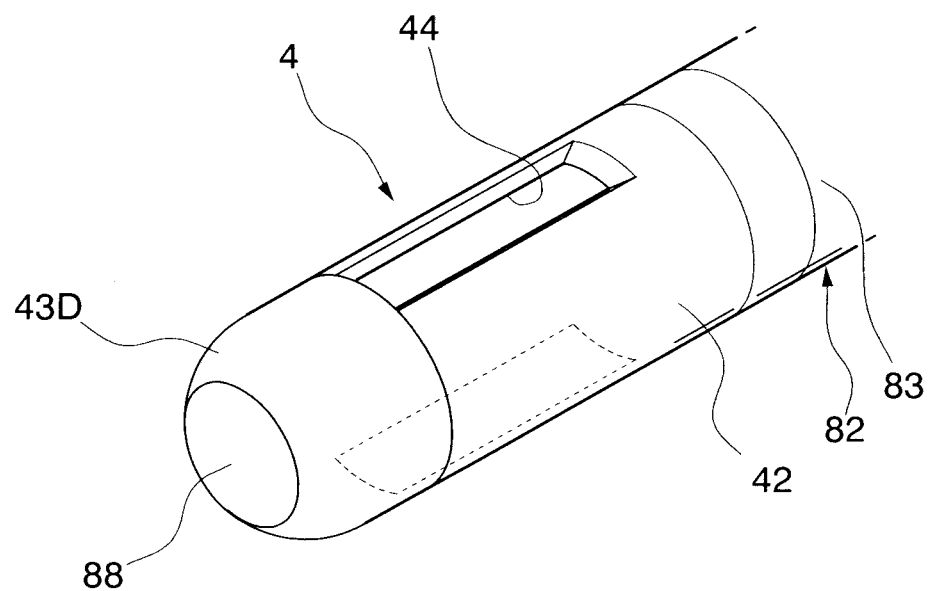
FIG. 20 is a perspective view illustrating a modified example of an ultrasonic sensor provided at the distal end of the cerclage instrument according to the third embodiment of the present invention.

As illustrated in FIG. 20, a distal end cap 43D having an ultrasonic sensor 88 (ultrasonic searcher) may be attached to the distal end of the main unit 42 of the cerclage instrument 4. The use of ultrasonic sensor 88 permits observation associated with traveling direction of the cerclage instrument 4 or the overtube 82; disposition of blood vessels in the gastric wall; observation of a space in the exterior of the stomach; and observation for other organs. Also, the thickness of mucosa or muscle coat of the gastric wall that undergoes cerclage can be measured by using the ultrasonic sensor 88.

Figure 21:
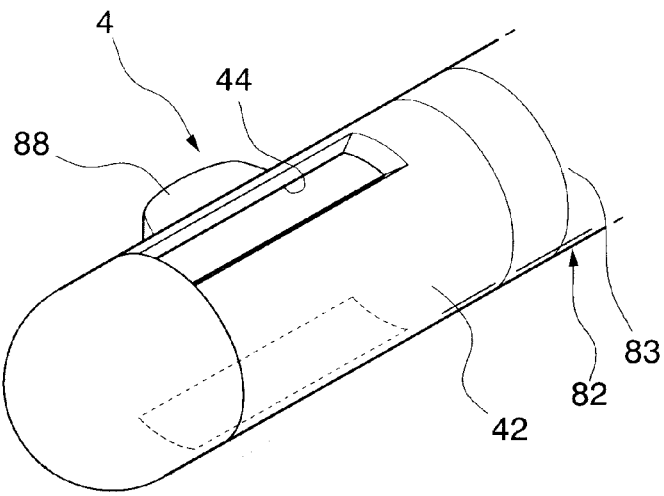
FIG. 21 is a perspective view illustrating a modified example of an ultrasonic sensor provided at a lateral side of the cerclage instrument according to the third embodiment of the present invention.
Figure 22:
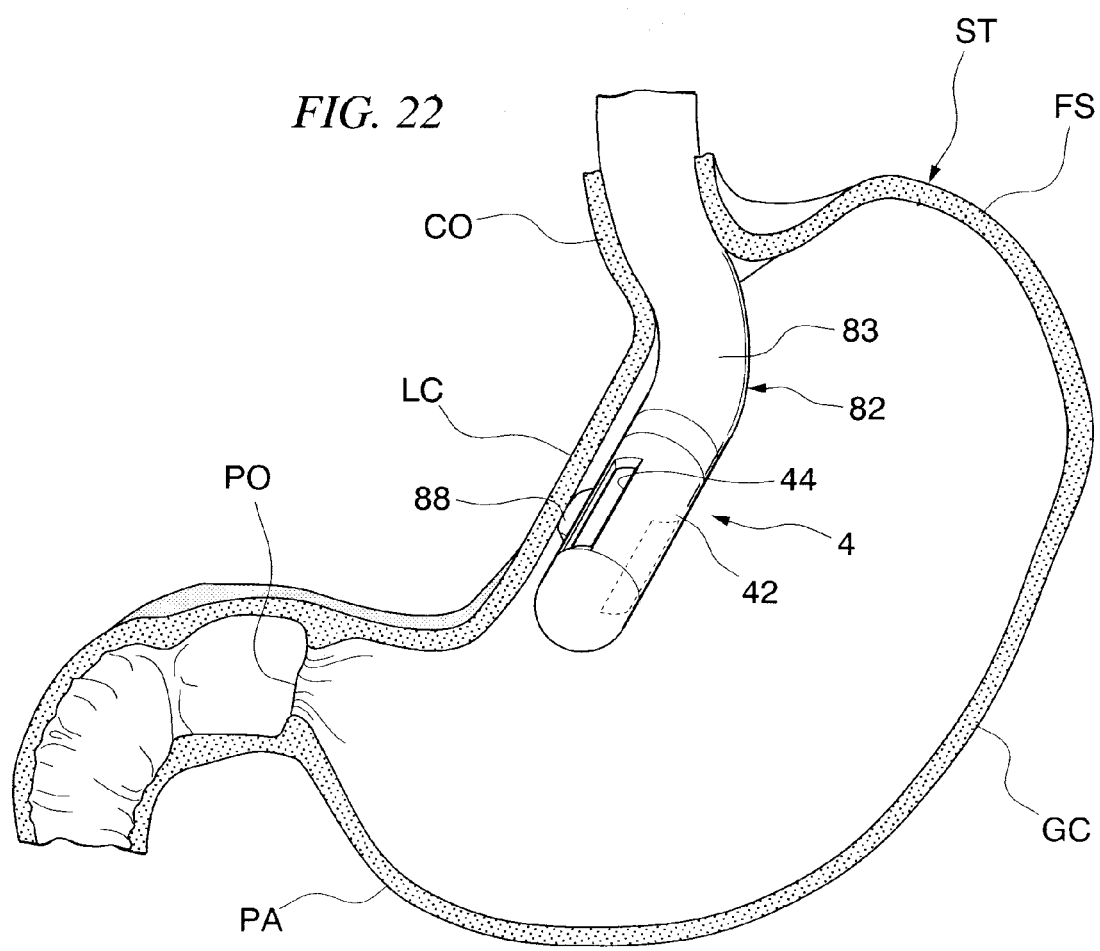
FIG. 22 is a schematic view illustrating how to advance the cerclage instrument according to the second embodiment of the present invention while the exterior of a gastric wall and a stomach are traced by an ultrasonic sensor.

As illustrated in FIG. 21, the ultrasonic sensor 88 may be attached to a lateral section of the main unit 42 of the cerclage instrument 4. The ultrasonic sensor 88 attached to the lateral section of the main unit 42 allows the overtube 82 to form a loop while tracing the lesser-curvature-line LC or the greater-curvature-line GC as illustrated in FIG. 22.

Figure 23:
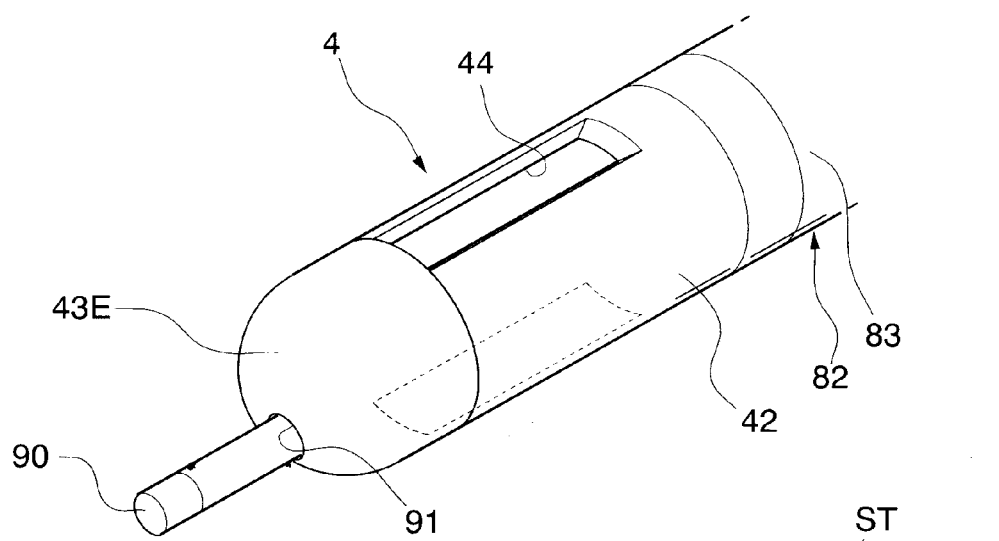
FIG. 23 is a perspective view illustrating a modified example of an ultrasonic probe according to the third embodiment of the present invention capable of freely projecting or retracting relative to the distal end of the cerclage instrument.

As illustrated in FIG. 23, a distal end cap 43E having a hole 91 that enables to project or retract an ultrasonic probe 90 may be attached to the distal end of the main unit 42 of the cerclage instrument 4.

Figure 24:
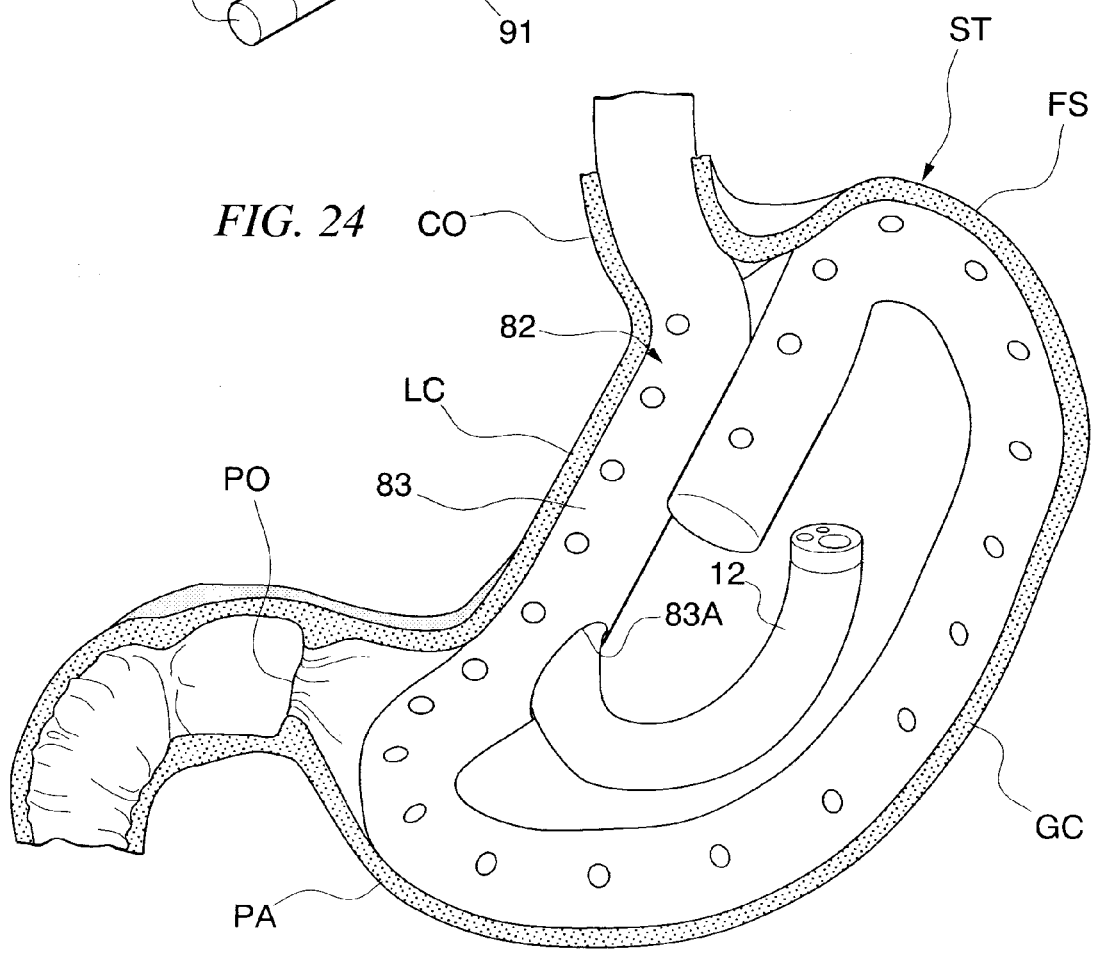
FIG. 24 is schematic view illustrating an endoscope according to the third embodiment of the present invention extending from a middle of the overtube looped in the stomach.

As illustrated in FIG. 24, a side hole 83A that enables to pass the insertion section 12 of the endoscope 2 therethrough may be formed on a lateral section of the main unit 83 of the overtube 82. The side hole 83A has an airtight valve that is not shown in the drawing. Formed on the periphery of the main unit 83 of the overtube 82 are a plurality of suction ports 84 that permit the air in the stomach ST to be suctioned therethrough. A cerclage instrument is passed through a job channel in the insertion section 12 of the endoscope 2 to cerclage a part of the stomach ST. Alternatively, the cerclage instrument 4 may be attached to the insertion section 12 in advance.

Fourth Embodiment

Figure 25:
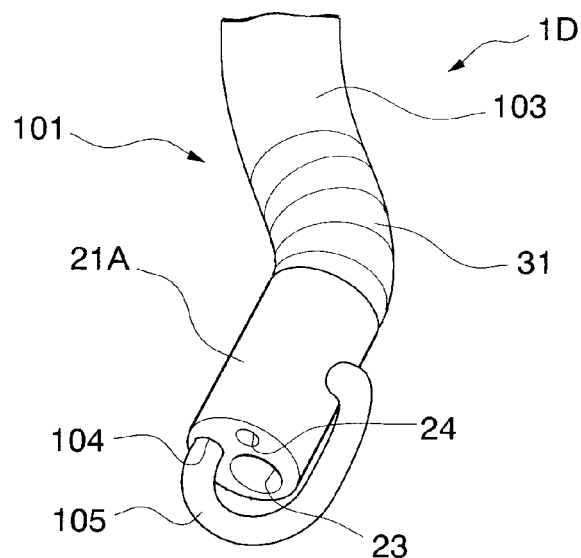
FIG. 25 is a perspective view illustrating an overtube according to a fourth embodiment of the present invention having a rod provided the distal end of the overtube.

As illustrated in FIG. 25, an opening section 104 of an inner lumen is provided on a distal end surface of a main unit 103 of an overtube 101 as a guide member in a therapy system 1D according to a fourth embodiment. A long length of elastic rod 105 is inserted through the overtube 101 so that the rod 105 is capable of extending or retracting therethrough. The rod 105 projects from the opening section 104. The rod 105 is operative as a loop-forming member. The distal end of the rod 105 is fixed to a lateral surface of the distal end section 21A of the main unit 103. The proximal end of the rod 105 is extracted from a manipulation section 22 of the overtube 101. The opening section 104 is disposed opposite the point where the distal end of the rod 105 is fixed relative to the opening section 23 of the other inner lumen.

Figure 26:
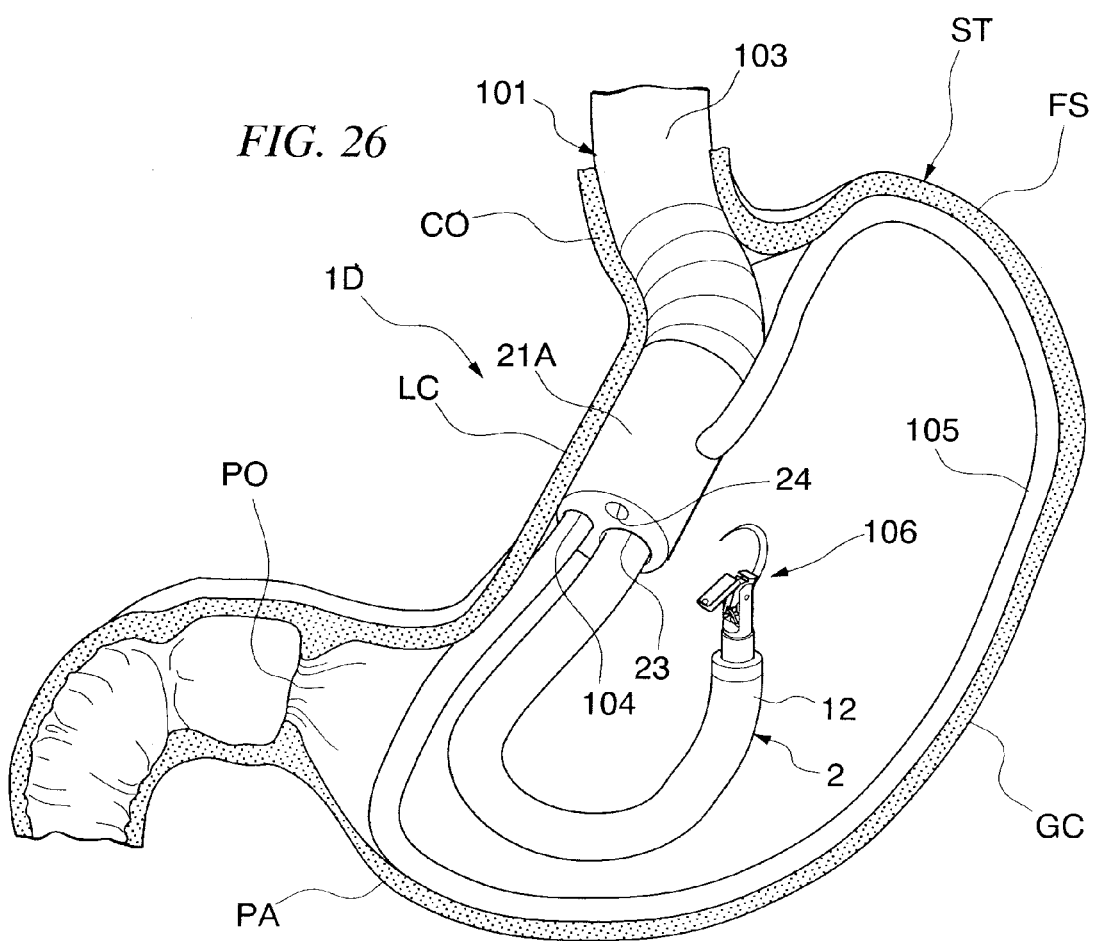
FIG. 26 is a schematic view of an expanded state of the rod according to the fourth embodiment of the present invention looped in the stomach.

The overtube 101 associated with therapeutic operation is inserted into a stomach ST from the mouth of a patient. The insertion of the overtube 101 into the stomach ST is adjusted so that the distal end section 21A enters the stomach ST. Furthermore, the direction of the distal end section 21A is adjusted so that the opening section 104 is disposed closer to the lesser-curvature-line LC; and the position where the distal end of the rod 105 is fixed is disposed closer to the greater-curvature-line GC. Subsequently, the rod 105 is pushed into the stomach ST while the overtube 101 is paused. The rod 105 forms a loop along the lesser-curvature-line LC and the greater-curvature-line GC as illustrated in FIG. 26 since the distal end of the rod 105 is fixed on the lateral surface of the distal end section 21A. Subsequently, air in the stomach ST is suctioned through a suction lumen 84 of the overtube 101. The stomach ST shrinks within the main unit 103 of the overtube 101 and the looped rod 105 so that the anterior wall FW is in proximity with the posterior wall RW. The shrink of the stomach ST imparts a substantial uniform tension to the anterior wall FW and the posterior wall RW of the stomach ST defined by the looped part of the rod 105; thus, the anterior wall FW overlaps the posterior wall RW in close contact. That is, the rod 105 serves as an arc member. The gastric wall is sutured by projecting the insertion section 12 of the endoscope 2 from the opening section 23 as illustrated in FIG. 26; and using a suture instrument 106 passed through the inner lumen in the insertion section 12 since the position of the anterior wall FW can be identified easily. In the present embodiment, the surgeon can acknowledge the accurate position to be cerclaged in the stomach ST; therefore, the therapeutic operation is facilitated. Also, a loop can be formed easily by pushing the rod 105 into the rod 105 and projecting the rod 105 from the opening section 104.

Figure 27:
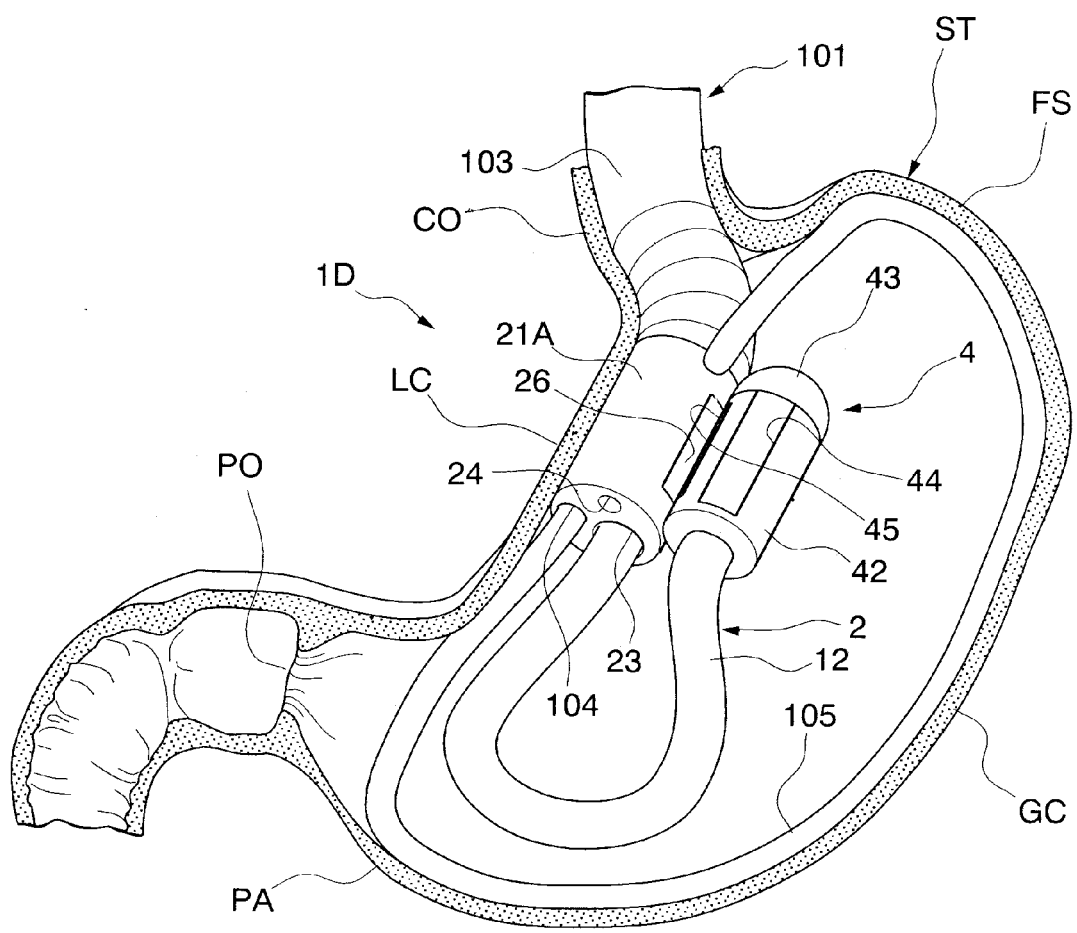
FIG. 27 is a schematic view illustrating how to use a cerclage instrument upon looping the rod in the stomach according to the fourth embodiment of the present invention.

In the present embodiment, the cerclage instrument 4 may be attached to the distal end of the insertion section 12 of the endoscope 2 as illustrated in FIG. 27, and the cerclage instrument 4 may be connected to the distal end section 21A of the overtube 101, since the insertion section 12 of the endoscope 2 does not have to form a loop. An example of a link apparatus provided to the overtube 101 is a Solenoid 26. A permanent magnet 45 is provided on the cerclage instrument 4 corresponding to the Solenoid 26.

Fifth Embodiment

Figure 28:
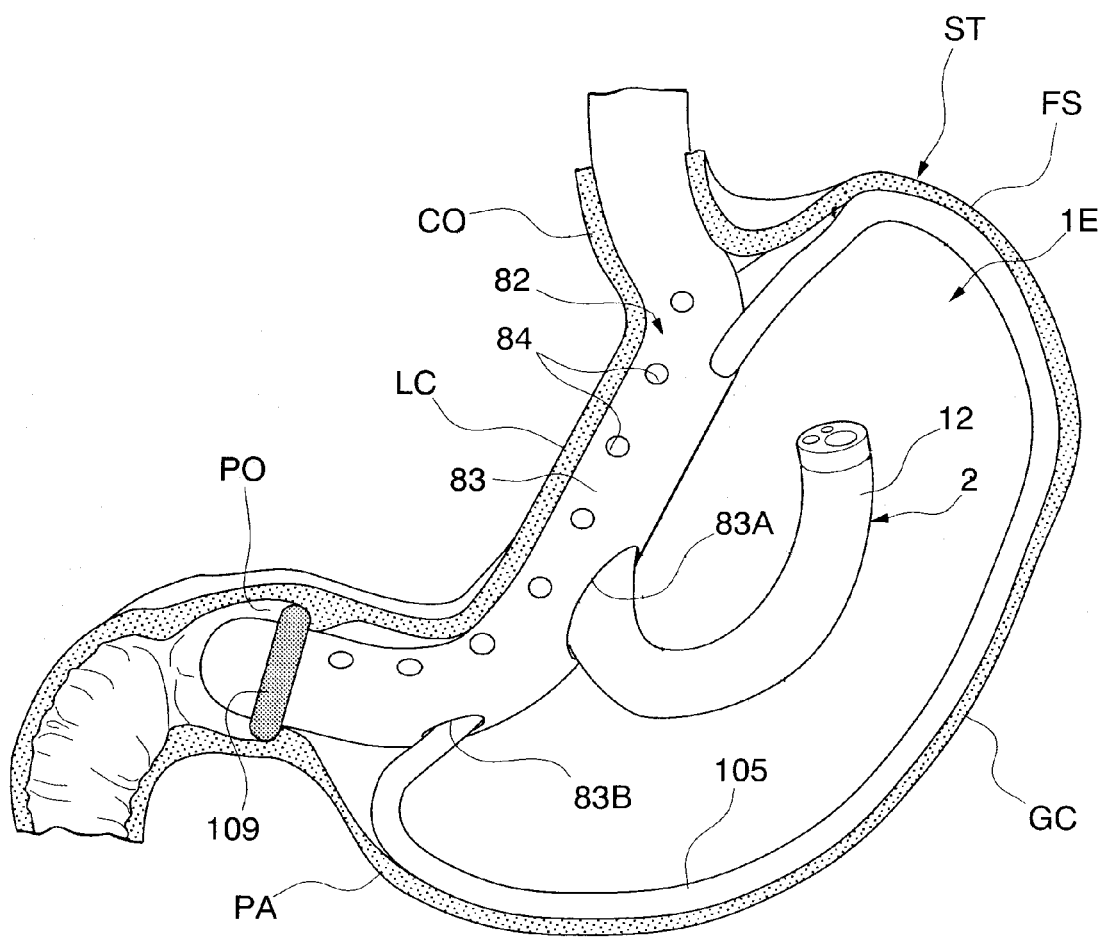
FIG. 28 is a perspective view illustrating an overtube having a balloon and a rod according to a fifth embodiment of the present invention.

As illustrated in FIG. 28, in a therapy system 1E according to a fifth embodiment, an opening section 83B that can allow a rod 105 to pass therethrough may be formed on a lateral section of a main unit 83 of a overtube 82 in the vicinity of the distal end of a main unit 83 relative to a side hole 83A. The rod 105 inserted and capable of freely advancing or retracting through the overtube 82 projects from the opening section 83B. Furthermore, a ring balloon 109 is attached to an outer periphery of the distal end section of the overtube 82.

Inflating the balloon 109 upon inserting the distal end section of the overtube 82 used for a therapeutic operation into a pylorus PO allows the overtube 82 to be fixed in the stomach ST. In addition, only air can be suctioned from the stomach ST since the pylorus PO is blocked by the balloon 109. A cerclage instrument 4 may be attached to an endoscope 2 in advance to cerclage a gastric wall by inserting a cerclage instrument, not shown in the drawing, into the stomach ST from the distal end of an insertion section 12 through a job channel of the endoscope 2. Bending the insertion section 12 of the endoscope 2 allows an arbitrary location of the stomach ST to be cerclaged. Also, positioning of the cerclage is facilitated.

Sixth Embodiment

In a sixth embodiment, a wall surface is cerclaged linearly in an organ.

Figure 29:
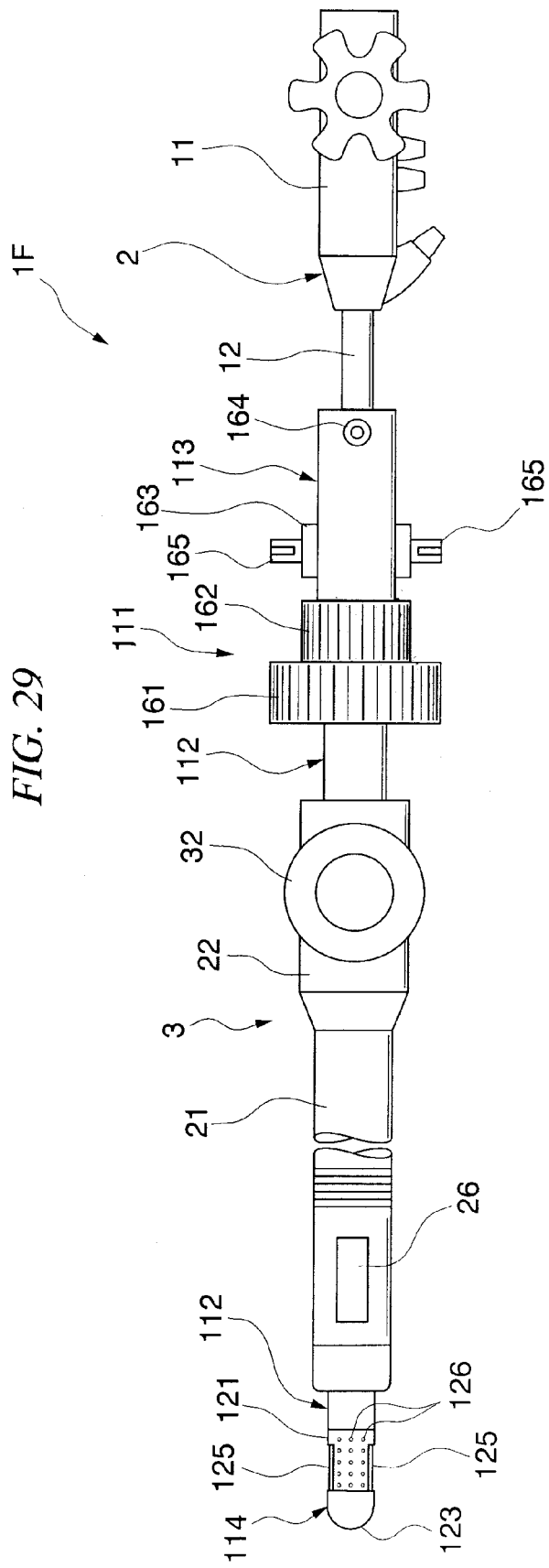
FIG. 29 is a perspective view illustrating an endoscope passing through an overtube, and a cerclage instrument according to a sixth embodiment of the present invention.

As illustrated in FIG. 29, a cerclage instrument 111 used in a therapy system 1F of the present embodiment is inserted through an overtube 3 that is a guide member. An endoscope 2 can be inserted into the cerclage instrument 111. The cerclage instrument 111 has a long length of elastic insertion section 112. The insertion section 112 is operative as a loop-forming member. A manipulation section 113 is provided on the proximal end of the insertion section 112. A hard therapy section 114 is provided on the distal end of the insertion section 112. The elastic insertion section 112 inserted through the overtube 3 as a guide member has a length that can form a loop in the stomach ST. The distal end of the insertion section 112 may be capable of bending if necessary. Specific configuration that enables the bending manipulation may be an insertion section 112 manufactured from a flexible material, or an assembly of corrugated tubes that is to be drawn by a wire. As illustrated in FIG. 13, each component 73a used in the corrugated tubes may have a cylindrical cross-section so that the insertion section 112 bends only along an arbitrary plane to form loop reliably. Also, as illustrated in FIG. 14, corrugated tubes 74 each having an elliptical cross-section may be employed to assure significant strength in a direction crossing to the bending direction. It should be noted that the cross-section of the corrugated tube is not limited to an ellipse, e.g., a deformed eclipse may be employed.

Figure 30:
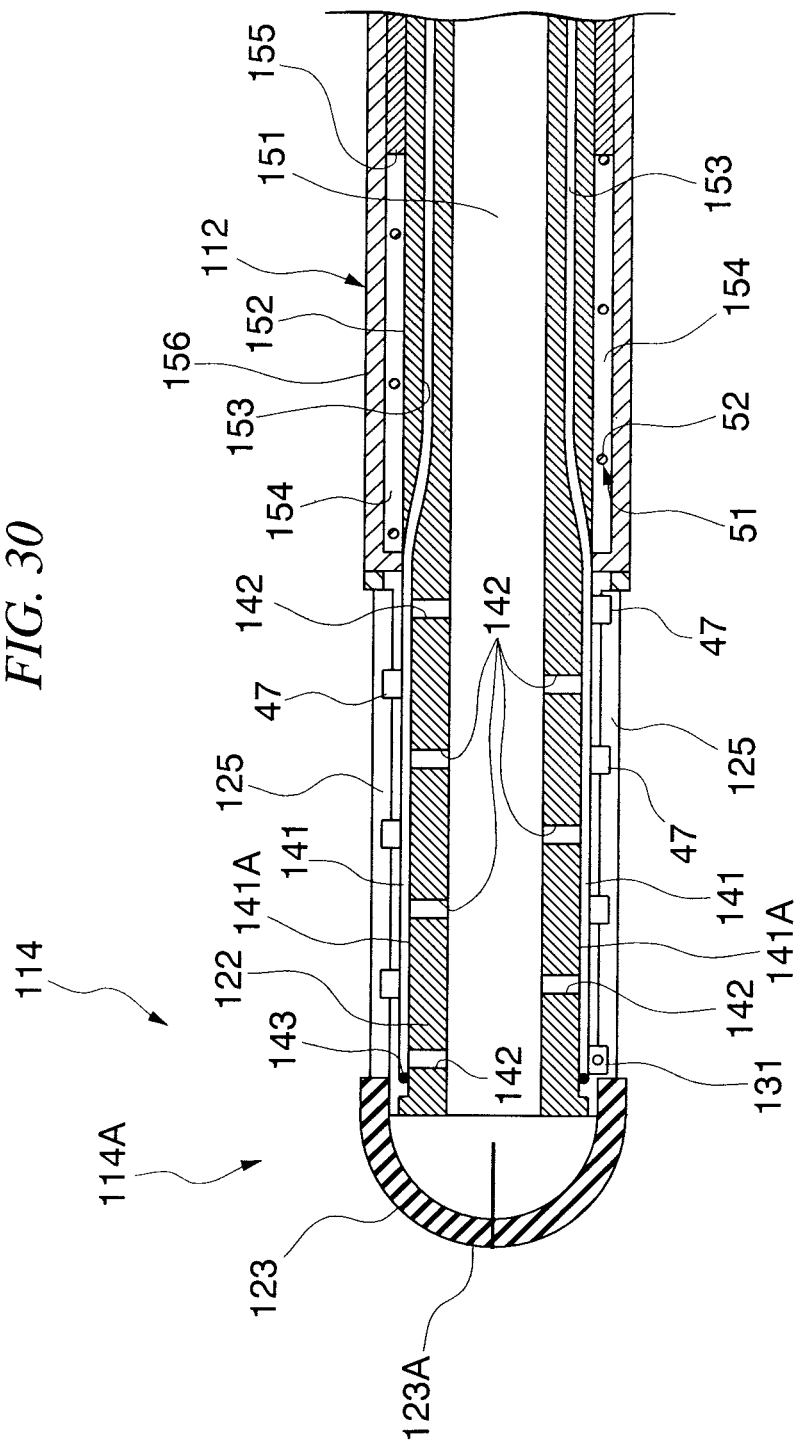
FIG. 30 is a cross-sectional view of the distal end of a cerclage instrument according to the sixth embodiment of the present invention.

As illustrated in FIGS. 29 and 30, a main unit 114A of the therapy section 114 has a dual-pipe structure constituted by a cylindrical outer cylinder 121 formed by an insulative material; and an inner cylinder 122 inserted through the outer cylinder 121. A distal end cap 123 is attached to the opening of the distal end of the outer cylinder 121. The size and transparency of the distal end cap 123 are significant for obtaining perspective of the observation device in the endoscope 2. A cross slit 123A is formed on the distal end cap 123. The use of distal end cap 123 allows the insertion section 12 of the endoscope 2 to project from the distal end of the therapy section 114 through the slit 123A.

Two side holes 125 as therapeutic windows are formed on lateral sections of the outer cylinder 121. The side holes 125 are disposed one by one symmetrically with respect to the central axis of the outer cylinder 121. Each side hole 125 is elongated in the central axis direction of the outer cylinder 121. A permanent magnet that serves as a link apparatus of the cerclage instrument 111 is attached to a portion of the outer cylinder 121 where the side holes 125 are not formed. The permanent magnet 45 is disposed on a right-hand side viewed in the direction toward the distal end from the proximal end of the overtube 3 so that one of the side holes 125 is disposed upward and the other one of the side holes 125 is disposed downwardly. That is, the permanent magnet 45 is disposed opposite the Solenoid 26 of the overtube 3. It should be noted that the link apparatus of the cerclage instrument 111 may be made from a magnetic member such as metal instead of the permanent magnet.

A plurality of holes 126 for suctioning an organ, e.g., a stomach ST are drilled on a section where the side holes 125 of the outer cylinder 121 or the permanent magnet are not provided.

Figure 31:
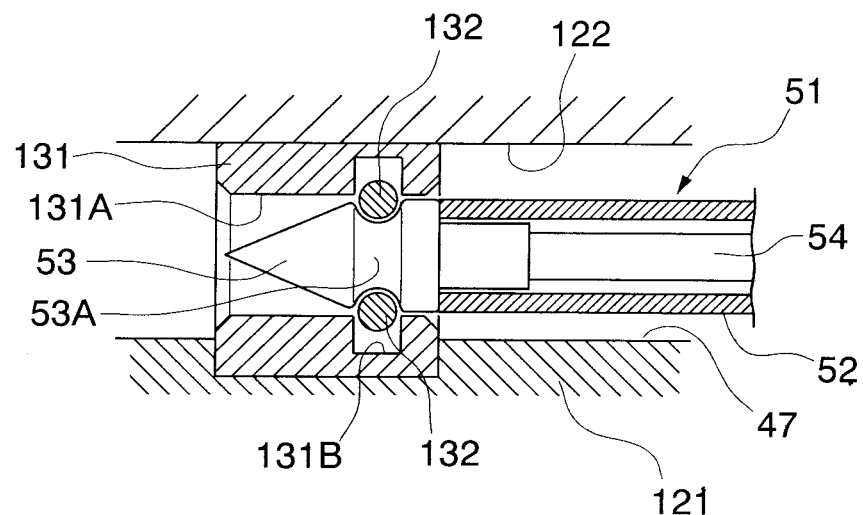
FIG. 31 is a cross-sectional view illustrating a catcher that receives a suture thread according to the sixth embodiment of the present invention.

A spiral groove 47 is formed on an inner surface of the outer cylinder 121. A spiral needle 51 serving as a tissue-cerclage instrument is passed through the groove 47. Alternatively, a spiral lumen may be formed in place of the groove 47. A radius of the spiral needle 51 in one round is smaller than a length obtained by adding the thickness of the muscle coat of the stomach to the radius of the inner cylinder 122. Therefore, when the suctioned gastric wall making close contact with the inner cylinder 122 is punctured, the spiral needle 51 inevitably punctures the inside of the muscle coat of the stomach, i.e., the spiral needle 51 never penetrates the gastric wall. The spiral needle 51 is constituted by a hollow and spirally-formed bending-needle section 52 consistent with the groove 47; and a needle distal end section 53 having an acute distal end. The needle distal end section 53 is detachably attached to the distal end of the bending-needle section 52. A suture thread, not shown in the drawing, is fixed, e.g., crimped onto the needle distal end section 53. The suture thread is passed through the bending-needle section 52. A catcher 131 that is a thread-releasing member for receiving a needle distal end section 53 is inserted in an end section of the groove 47 on the distal end section of the therapy section 114. As illustrated in FIG. 31, the catcher 131 has a groove 131A that allows the needle distal end section 53 to be inserted therethrough. A spring 132 capable of engaging with a reduced-diameter section 53A of the needle distal end section 53 is enclosed in a housing 131B in a middle of the groove 131A. The U-letter-shaped spring 132 is disposed so that a pair of end sections pass through the groove 131A. The housing 131B has an extra space so that the pair of end sections of the spring 132 may increase in width in a direction orthogonal to a direction for inserting the needle distal end section 53.

Figure 32:
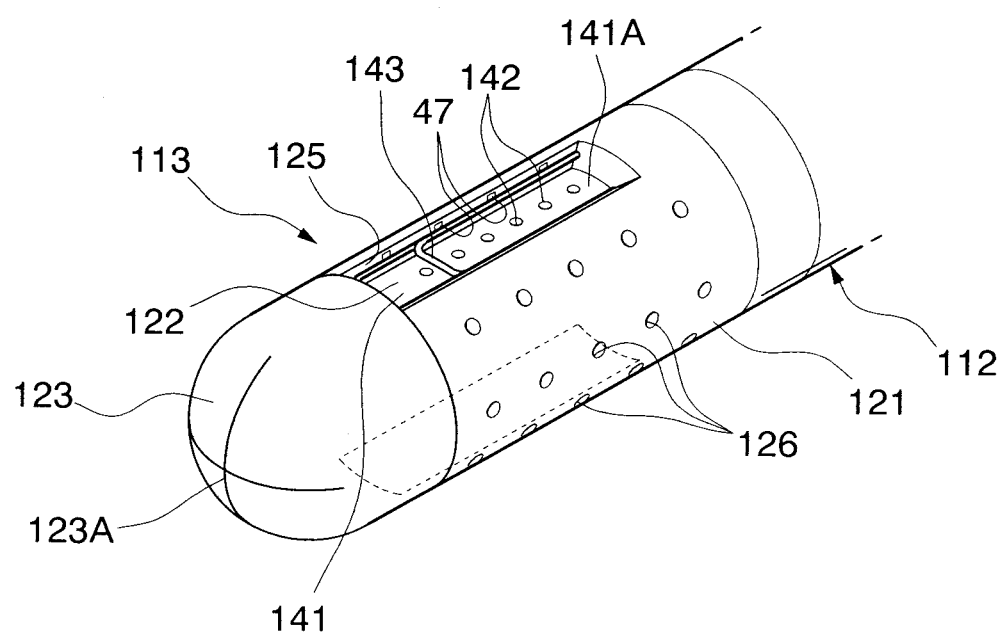
FIG. 32 is a perspective view illustrating a therapy section according to the sixth embodiment of the present invention.

As illustrated in FIGS. 29 and 30, a pair of grooves 141 are formed on an outer periphery of the inner cylinder 122. A plurality of suction holes 142 are formed on a bottom surface 141A of the groove 141. Furthermore, each groove 141 has an electrode wire 143 as a tissue-dissecting instrument embedded thereon. As illustrated in FIG. 32, the electrode wire 143 is a piece of conductive wire that is bent in a substantial U-letter shape. The bent part of the electrode wire 143 is disposed to traverse the groove 141. The half parts extending in parallel are disposed along the lateral surfaces that face each other of the groove 141, and extracted to the cerclage instrument 111 proximally. The bottom surface 141A of the groove 141 is formed so that the electrode wire 143 is positioned in a substantial midpoint between the mucosa and the muscle coat when the anterior wall FW or the posterior wall RW of the stomach ST is retracted into the groove 141 to cause the mucosa of the stomach to make close contact with the bottom surface 141A. Preparing therapy sections 114 having different depths of the bottom surface 141A and exchanging the therapy section 114 corresponding to the thickness of the mucosa that undergoes a treatment allow an arbitrary thickness of mucosa to be dissected reliably. It should be noted that the suction holes 142 are formed on a section of the inner cylinder 122 where the groove 141 is not formed.

As illustrated in FIG. 30, an elastic insertion section 112 has a dual-pipe structure. The endoscope 2 can freely advance or retract through the inner hole 151 of the insertion section 112. A cylinder section 152 is an elastic insulative pipe that is integrated with the inner cylinder 122 of the therapy section 114. A pair of lumens 153 are capable of freely advancing or retracting through the cylinder section 152. A part of the spiral needle 51 is housed in the ring space 154 between the outer cylinder 156 and the inner cylinder 122, and in addition, a torque tube 155 that transmits a torque to the spiral needle 51 is passed through the space 154.

Figure 33:
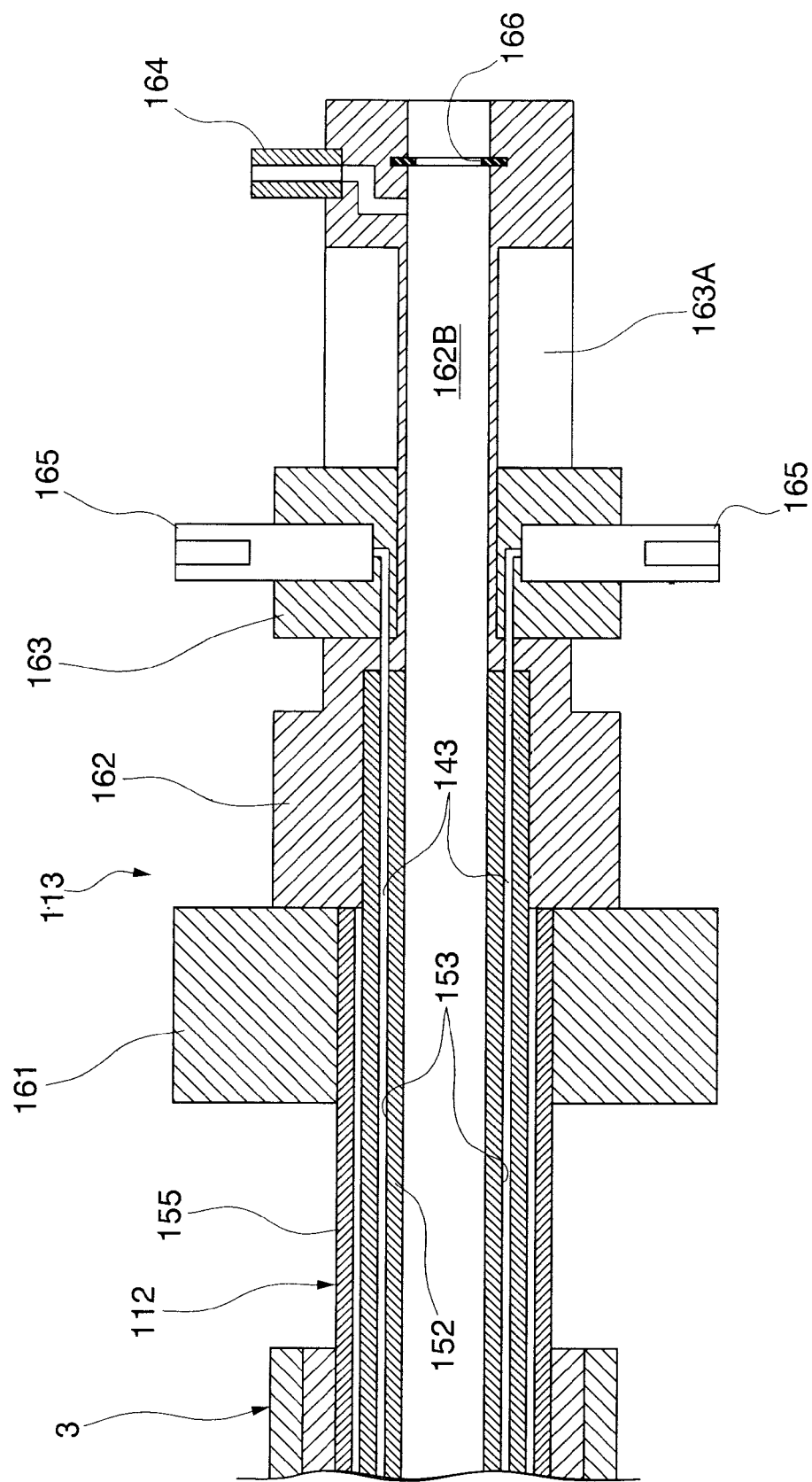
FIG. 33 is a cross-sectional view of a maneuvering section according to the sixth embodiment of the present invention.

As illustrated in FIGS. 29 and 33, provided in distal-to-proximal order are: a spiral-needle-rotating knob 161; an inner cylinder knob 162; an electrode-maneuvering knob 163; and a suction mouthpiece 164. A torque tube 155 is fixed to the spiral-needle-rotating knob 161. A cylinder section 152 is fixed to the inner cylinder knob 162. The electrode-maneuvering knob 163 capable of freely advancing or retracting is disposed in the groove 163A formed on the inner cylinder knob 162. A pair of connectors 165 are provided to the electrode-maneuvering knob 163. The electrode wire 143 extracted from the lumen 153 is connected to each connector 165. A high-frequency power supply, that is not shown in the drawings, is connected to the connectors 165. The suction mouthpiece 164 communicates to the inner hole 162B of the inner cylinder knob 162. A ring seal member 166 disposed in a proximal section of the manipulation section 113 relative to the suction mouthpiece 164 maintains airtightness when the endoscope 2 is inserted through the inner hole 162B.

Therapeutic operation in the present embodiment is explained. A thickness of the gastric wall is measured in prior to cerclaging the stomach. A thickness of a mucosa of a gastric wall that undergoes a cerclage and a thickness of a muscle coat of the gastric wall are measured upon inserting a gastric wall-measuring apparatus into the stomach. A preferable stomach-wall-measuring apparatus is an ultrasonic endoscope, etc.

In order to dissect the mucosa of the stomach or to cerclage the muscle coat of the stomach reliably, a cerclage instrument 111 that corresponds to the measured thickness of the mucosa or the muscle coat is chosen. Alternatively, an inner cylinder of the cerclage instrument 111 is exchanged to adjust a position for fixing the mucosa or the muscle coat of the stomach.

The cerclage instrument 111 is passed through the overtube 3 and the endoscope 2 is passed through the cerclage instrument 111 prior to cerclage a part of the stomach ST. The distal end of the endoscope 2 inserted into the therapy section 114 is further projected from the distal end of the distal end cap 123 through a cross slit 123A. Consequently, the overtube 3 is introduced into the stomach ST while observing therearound by the observation device of the endoscope 2.

Figure 34:
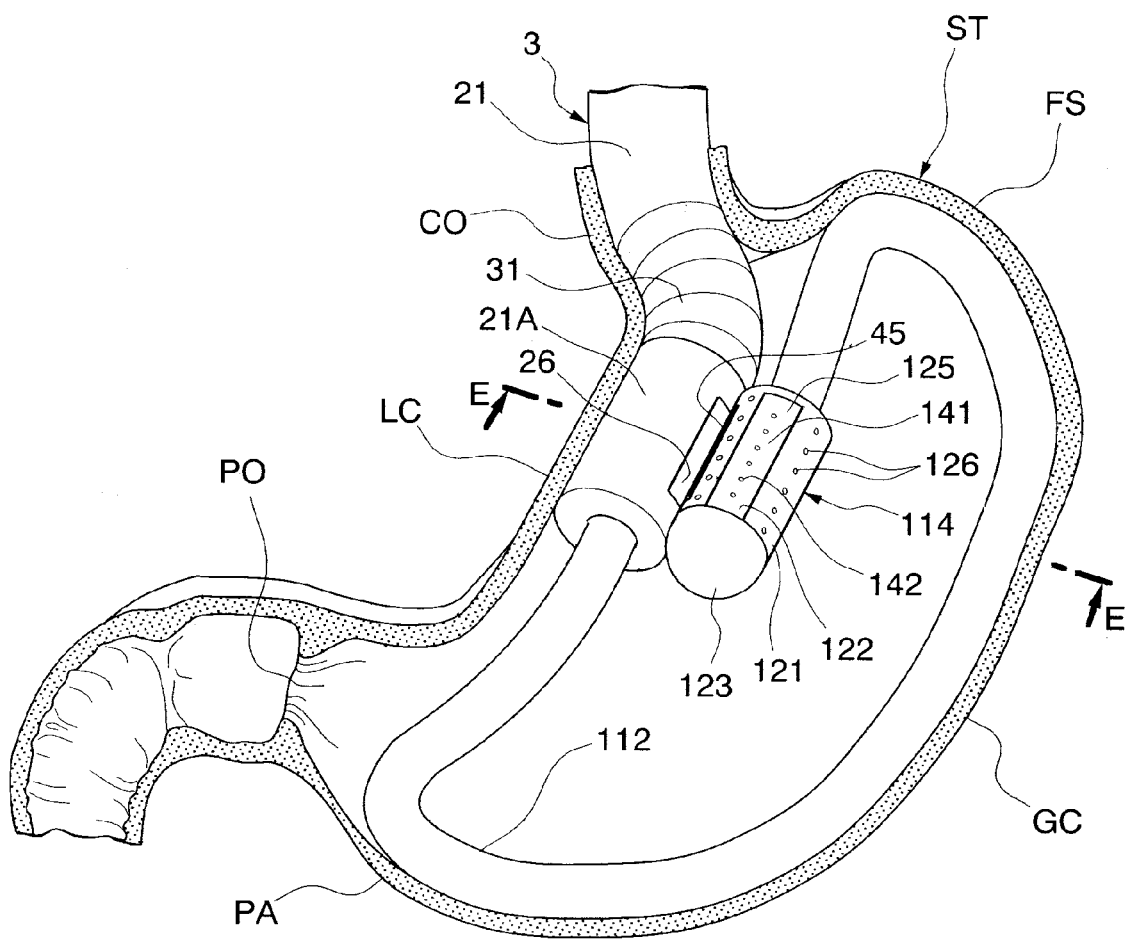
FIG. 34 is a schematic view of an insertion section of the cerclage instrument looped in the stomach according to the sixth embodiment of the present invention.

As illustrated in FIG. 34, the overtube 3 is paused when a predetermined portion of the distal end section 21A of the overtube 3 enters the stomach. Consequently, the insertion of the overtube 3 is adjusted so that the bending section 31 reaches to the vicinity of a cardia CO; and so that the distal end section 21A is about to enter the stomach ST. Furthermore, the Solenoid 26 is adjusted to be directed toward the greater-curvature-line GC of the stomach ST. The distal end section 21A is disposed along the lesser-curvature-line LC when the inserted overtube 3 is disposed by manipulating the bending handle 32 of the manipulation section 22 while observing an image inside of a patient obtained through a distal end cap 43 of the cerclage instrument 111 by using the observation device of the endoscope 2.

The insertion section 112 and the therapy section 114 of the cerclage instrument 111 are projected from the overtube 3 upon disposing the Solenoid 26 to be directed toward the greater-curvature-line GC and fixing the overtube 3. The insertion section 112 and the therapy section 114 advance along the lesser-curvature-line LC of stomach ST toward the pyloric antrum PA, and hit the gastric wall in the vicinity of the pyloric antrum PA. The insertion section 112 and the therapy section 114 upon hitting the gastric wall return along the greater-curvature-line GC of the stomach ST and travel further. Consequently, the insertion section 112 and the therapy section 114 return again in the vicinity of the gastric fundus FS to form a loop. Meanwhile, the endoscope 2 is retracted in the therapy section 114.

Accordingly, as illustrated in FIG. 34, the insertion section 112 and the therapy section 114 project from the overtube 3 in the vicinity of the cardia CO; travel along the lesser-curvature-line LC, the greater-curvature-line GC, and the gastric fundus FS; and return to the vicinity of the distal end section 21A of the overtube 3. The insertion section 112 thus forms a loop. The therapy section 114 upon returning to the vicinity of the distal end section 21A is disposed in proximity with the Solenoid 26 disposed at the distal end section 21A of the overtube 3 in the stomach ST. Turning on the Solenoid switch causes electricity to flow in the Solenoid 26, thereby absorbing the permanent magnet 45. Accordingly, the lateral surface of the overtube 3 is joined to the lateral surface of the cerclage instrument 111.

In a case where the link apparatus of the overtube 3 uses a permanent magnet, the cerclage instrument 111 in proximity with the distal end section 21A of the overtube 3 is automatically absorbed. Accordingly, as illustrated in FIG. 34, one of the pair of side holes 125 of the therapy section 114 is disposed to be directed toward the anterior wall FW, and the other one of the side holes 125 is disposed to be directed toward the posterior wall RW. Suctioning air from the stomach ST through the suction lumen 24 of the overtube 3 causes the stomach ST to be shrunk so that the anterior wall FW starting from the lesser-curvature-line LC and the greater-curvature-line GC overlaps the posterior wall RW. The looped section of the insertion section 112 imparts a substantial uniform tension to the anterior wall FW and the posterior wall RW of the stomach ST; thus, the anterior wall FW overlaps the posterior wall RW in close contact. That is, the insertion section 112 serves as an arc member. In a case where the patient is lying on his or her back, the anterior wall FW of the stomach ST is disposed on a looped portion of the insertion section 112; and the posterior wall RW is disposed under the looped portion. The side hole 125 makes a substantial close contact with the anterior wall FW, and the other side hole 125 makes a substantial close contact with the posterior wall RW.

Figure 35:
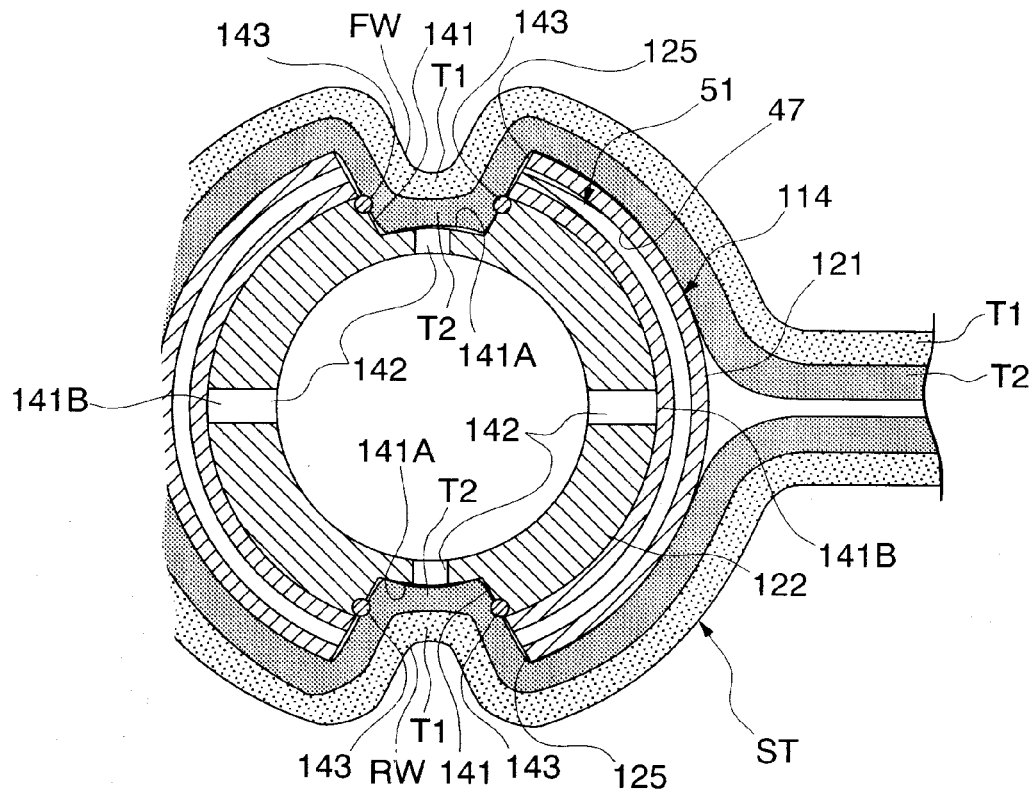
FIG. 35 is a cross-sectional view viewed along E-E line of FIG. 34 illustrating a mucosa suctioned into the cerclage instrument according to the sixth embodiment of the present invention.

Air in the cerclage instrument 111 is suctioned by a suction apparatus, not shown in the drawing, connected to a suction mouthpiece 164 of the cerclage instrument 111. Accordingly, two points of the gastric wall, i.e., the anterior wall FW and the posterior wall RW are suctioned through the side hole 125 and the suction hole 142. As illustrated in FIG. 35, the anterior wall FW and the posterior wall RW suctioned into the two grooves 141 respectively make close contact with the bottom surface 141A of the groove 141. This causes a biomedical tissue retracted into the pair of the side holes 125 to be fixed on the bottom surface 141A. The electrode-maneuvering knob 163 is retracted while high-frequency electric current is charged to the electrode wire 143 through a connector 165 of the electrode-maneuvering knob 163. The mucosa of the anterior wall FW and the mucosa of the posterior wall RW retracted into the groove 141 respectively are dissected by the electrode wire 143 since the groove 141 is optimized to have a depth suitable for the thickness of the mucosa, and since a height of the electrode wire 143 from the bottom surface 141A is adjusted to be disposed at a substantial midpoint between the mucosa and the muscle coat.

Figure 36:
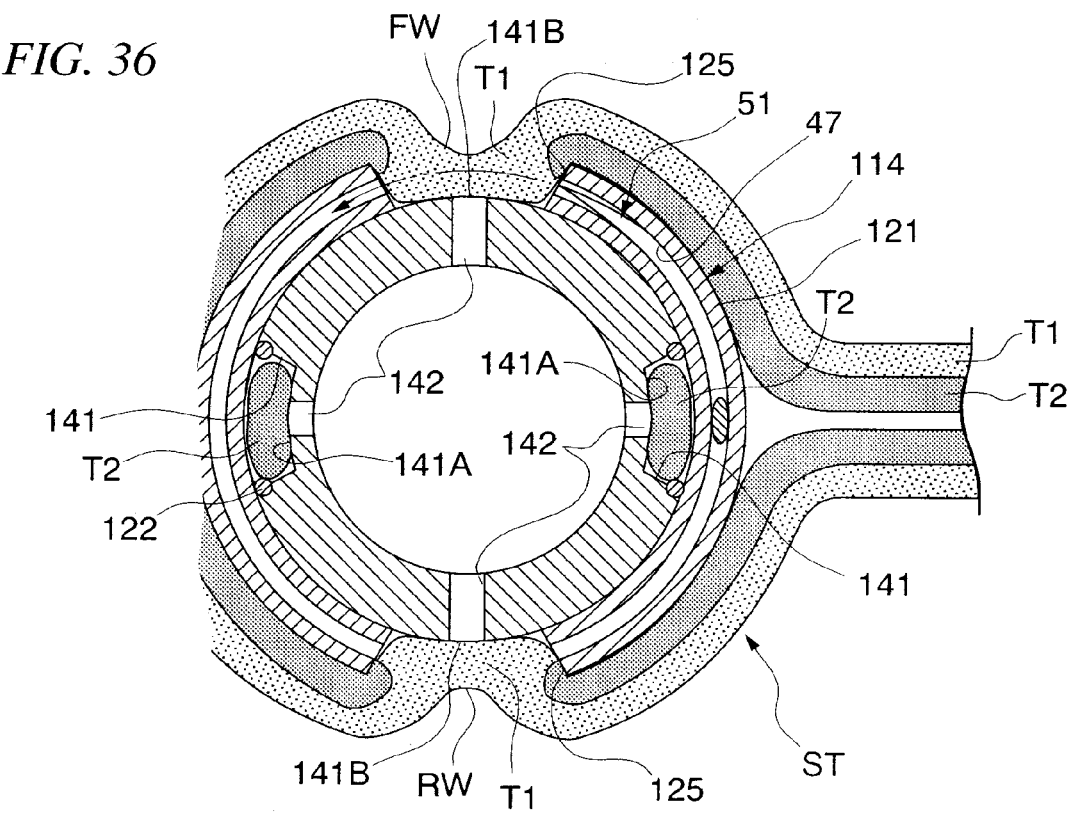
FIG. 36 is a cross-sectional view illustrating a rotated state of an inner cylinder section upon dissecting the mucosa illustrated in FIG. 35 according to the sixth embodiment of the present invention.

The charging of the high-frequency electric current is paused after dissecting the mucosa, and then the inner cylinder knob 162 is rotated. As illustrated in FIG. 36, the dissected mucosa rotates together with the groove 141; thus, the mucosa is removed from the muscle coat. Rotating the inner cylinder 122 until the suction hole 142 of the inner cylinder 122 is exposed from the side hole 125 causes the muscle coat of the gastric wall that has undergone the mucosa dissection to be suctioned through the side holes 125 and the suction hole 142. This results in fixing the muscle coat of the gastric wall retracted from the pair of the side holes 125 on the outer peripheral surface 141B of the inner cylinder 122.

Figure 37:
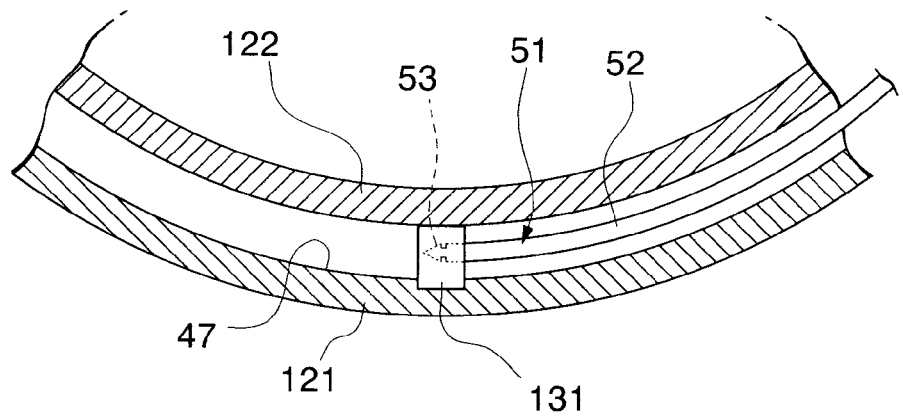
FIG. 37 is a perspective view illustrating a spiral needle captured by a catcher according to the sixth embodiment of the present invention.
Figure 38:
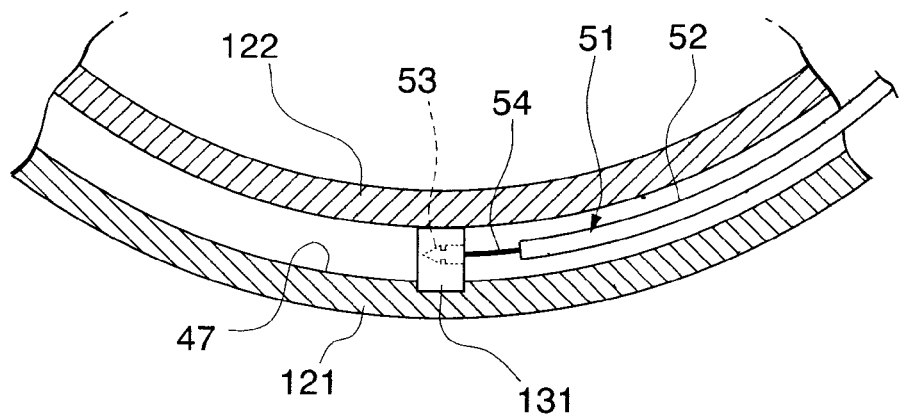
FIG. 38 is a schematic view illustrating a needle's distal end removed from a needle section upon retracting the spiral needle illustrated in FIG. 37.

Rotating and advancing the spiral-needle-rotating knob 161 cause the spiral needle 51 joined to the spiral-needle-rotating knob 161 through the torque tube 155 to be advanced along the groove 47 while being rotated in a spiral direction. The spiral needle 51 does not enter an abdominal cavity since a radius of the spiral needle 51 in one round is smaller than a length obtained by adding the thickness of the muscle coat of the stomach to the radius of the inner cylinder 122, and since the spiral needle 51 traversing the side holes 125 alternately penetrates the muscle coat of the anterior wall FW and the muscle coat of the posterior wall RW that are retracted into the side holes 125 to make close contact with the inner cylinder 122. Advancing the spiral needle 51 to the distal end of the groove 47 causes the needle distal end section 53 to enter a groove 131A while pushing the spring 132 of the catcher 131 outwardly along a taper surface; thus, the spiral needle 51 received by the catcher 131 is paused as illustrated in FIG. 37. Consequently, retracting the spiral-needle-rotating knob 161 while rotating the spiral-needle-rotating knob 161 in the reverse direction causes the spiral needle 51 to be returned along the groove 47. However, the needle distal end section 53 does not move because the needle distal end section 53 is retained by the catcher 131, and because the catcher 131 is supported by the groove 47 and the inner cylinder 122. Therefore, only the needle distal end section 53 is removed from the bending-needle section 52 as illustrated in FIG. 38. This results in that the suture thread 54 passing through the bending-needle section 52 still remains but the bending-needle section 52 is removed from the anterior wall FW and the posterior wall RW.

Figure 39:
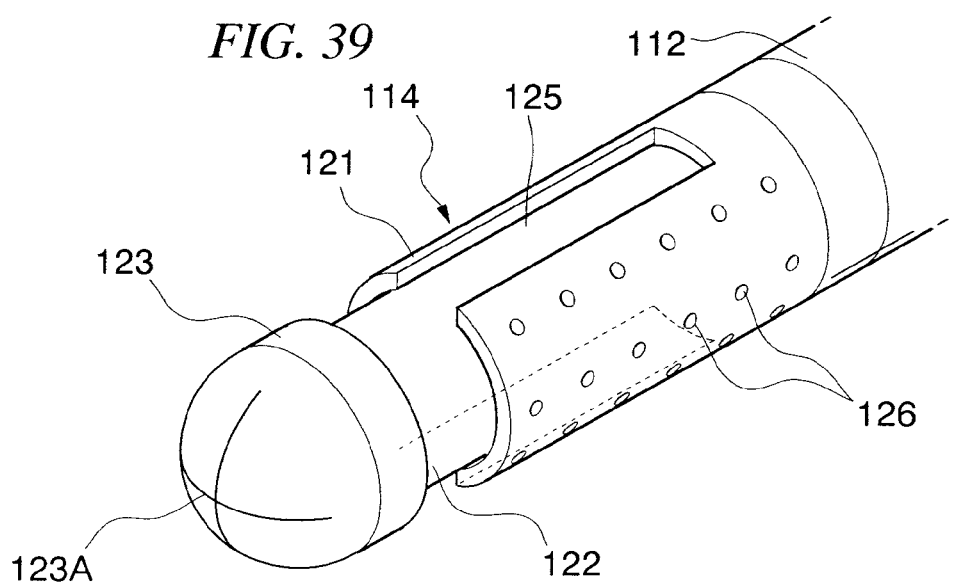
FIG. 39 is a perspective view illustrating a distal end cap removed from an outer cylinder by advancing an inner cylinder section according to the sixth embodiment of the present invention.
Figure 40:
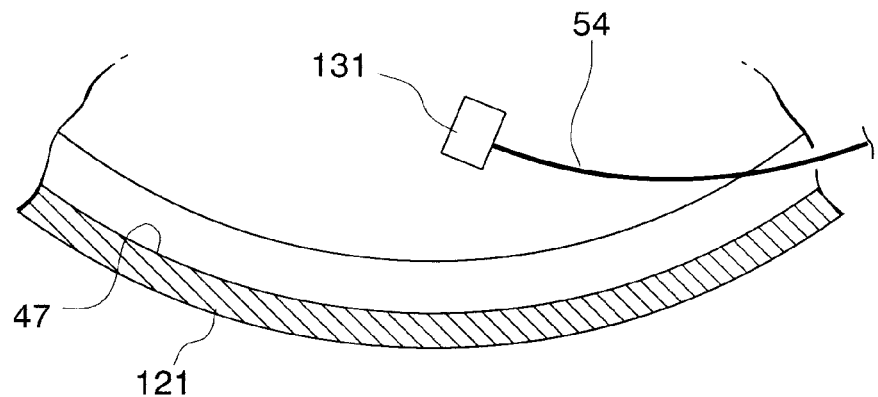
FIG. 40 is a perspective view illustrating the catcher detached from the outer cylinder section by retracting the inner cylinder section according to the sixth embodiment of the present invention.
Figure 41:
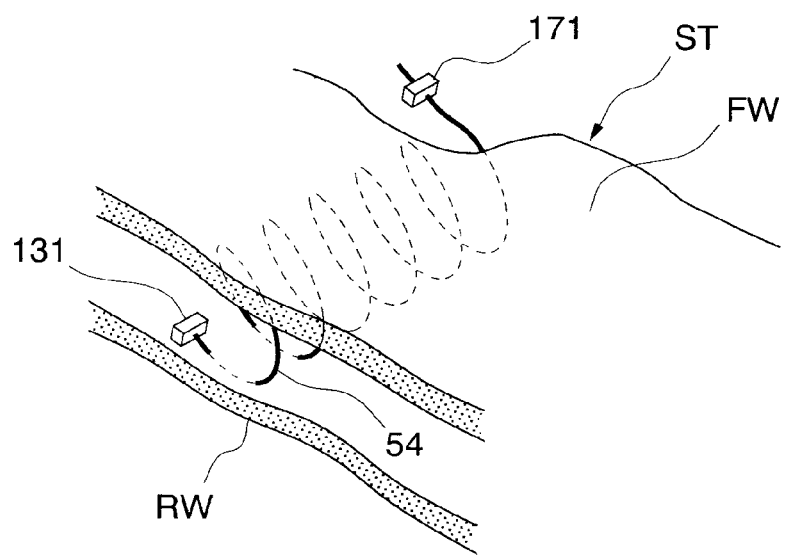
FIG. 41 illustrates the cerclage instrument removed from the stomach upon cerclaging the gastric wall according to the sixth embodiment of the present invention.

The distal end cap 123 is pushed by using the endoscope 2 or the inner cylinder 122 upon removing the bending-needle section 52 from the muscle coat. This causes the distal end cap 123 to be removed from the outer cylinder 121 as illustrated in FIG. 39. The distal end cap 123 is collected by using the endoscope 2. Subsequently, retracting and rotating the inner cylinder knob 162 causes the catcher 131 that has been pushed by the inner cylinder 122 to be removed from the outer cylinder 121 as illustrated in FIG. 40. Fully retracting the cerclage instrument 111 causes the cerclaged tissue to get out of a released end of the distal end of the side hole 125. Constricting the tissue by a stopper 171 attached to an end section of the suture thread 54 causes the anterior wall FW and the posterior wall RW of the stomach ST to be cerclaged as illustrated in FIG. 41. The cerclaged and closely contacting section is easy to adhere since the mucosa is dissected by using the electrode wire 143.

The section cerclaged by the suture thread 54 forms a substantial cylindrical passway that extends from the cardia CO to the pylorus PO in the stomach ST as illustrated in FIG. 10. One can expect to prevent obesity since the constricted part of the stomach ST, specifically the vicinity of the cardia CO that undertakes incoming food, hinders the stomach ST from intaking a significant amount of food.

The present embodiment can shrink the stomach ST so that the anterior wall FW makes close contact with the posterior wall RW when the insertion section 112 is pushed along the lesser-curvature-line LC and the greater-curvature-line GC into the stomach ST and then the air is suctioned from the stomach ST. Accordingly, the surgeon can acknowledge the accurate position to be cerclaged in the stomach ST; thereby facilitating the therapeutic operation.

The gastric wall can be cerclaged by retracting the anterior wall FW and the posterior wall RW of the stomach ST into the cerclage instrument 111; rotating the spiral needle 51; and using the suture thread 54 in the stomach ST. The therapeutic operation is easy, because procedures are simple and a complex apparatus is not necessary. An arbitrary position of the gastric wall can be cerclaged reliably since the position of the cerclage instrument 111 is stabilized by using the Solenoid 26 and the permanent magnet.

A diameter of the substantial cylindrical cerclaged passway can be the same as an outer diameter of the overtube 3 or greater than that. Therefore, a desirable size of passway can be formed when a narrow overtube 3 is used.

In the present embodiment, the muscle coats make close contact with each other since the long length of the cerclaged section is dissected from the muscle coat. This facilitates an adhesion between the anterior wall FW and the posterior wall RW, thereby cerclaging a part of the stomach ST more reliably. Also, dissecting of mucosa and suturing a thread into the muscle coat can be conducted while the tissue suctioned and fixed into the side holes 125 is maintained. Only rotating the inner cylinder 122 can transit from fixture by a tissue by a first gastric-wall-fixing section to fixture by a second gastric-wall-fixing section where the first gastric-wall-fixing section indicates the bottom surface 141A of the groove 141; and the second gastric-wall-fixing section indicates the outer peripheral surface 141B. This facilitates exposing a section of the muscle coat by removing the dissected mucosa.

The needle distal end section 53 is not necessary to be collected temporarily since the distal end section of the spiral needle 51 is housed in the catcher 131. The tissue can be bound easily by using the catcher 131 as an anchor.

Figure 42:
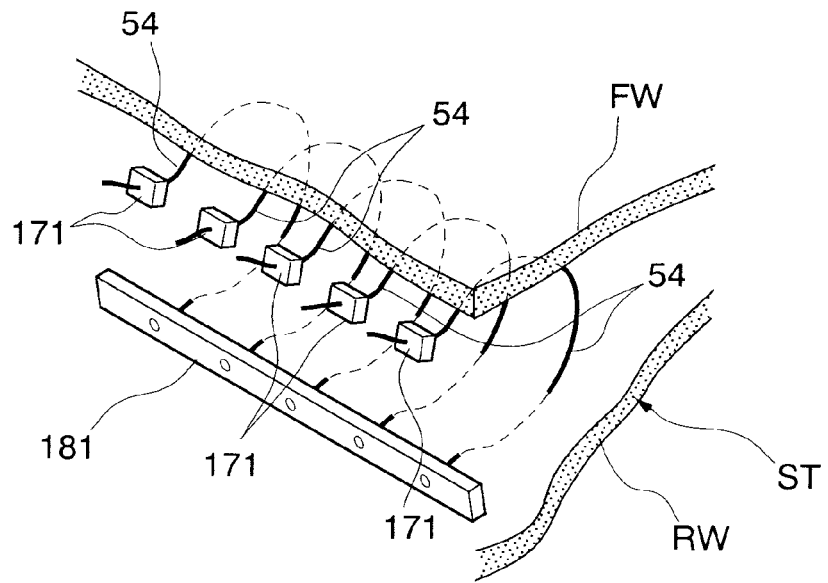
FIG. 42 is a schematic view of another cerclage sate conducted by using a plurality of suture threads according to the sixth embodiment of the present invention.

In the present embodiment, the previously-explained ultrasonic sensor may be attached to the cerclage instrument 111; or the ultrasonic probe capable of freely projecting or retracting may be provided. FIG. 42 shows an example where a tissue is cerclaged by using a cerclage instrument having a different structure from that of the above explained structure. A plurality of parallelly disposed suture threads 54 are passed through the anterior wall FW and the posterior wall RW. A needle distal end of each suture thread 54 is connected to a catcher 181. Grooves, housing sections, and springs in the same number as the number of the needles distal ends are provided to the catcher 181 at a predetermined intervals. The cerclage instrument as illustrated in FIG. 42 has a plurality of C-letter-shaped suture needles in place of spiral threads. Rotating the plurality of suture threads allows the suture threads to puncture into the muscle coat of the anterior wall FW and the muscle coat of the posterior wall RW alternately. Cerclaging is not limited to the use of a needle and thread; that is, cerclaging may use a fastener, a stapler, a clip, a tag, a T-bar, or a clamp, etc.

As illustrated in FIG. 11, the link apparatus may be constituted by a recessed section 61 provided to the distal end section 21A of the overtube 3; and a projecting section 62 provided to the cerclage instrument 4. Preferably, the recessed section 61 and the projecting section 62 should be fit to each other; and the both components should be connected or separated easily by sliding them in an axial line direction. Providing the recessed section to the overtube 3 facilitates the insertion into the body while the recessed section may be provided to the cerclage instrument 4.

Seventh Embodiment

Figure 43:
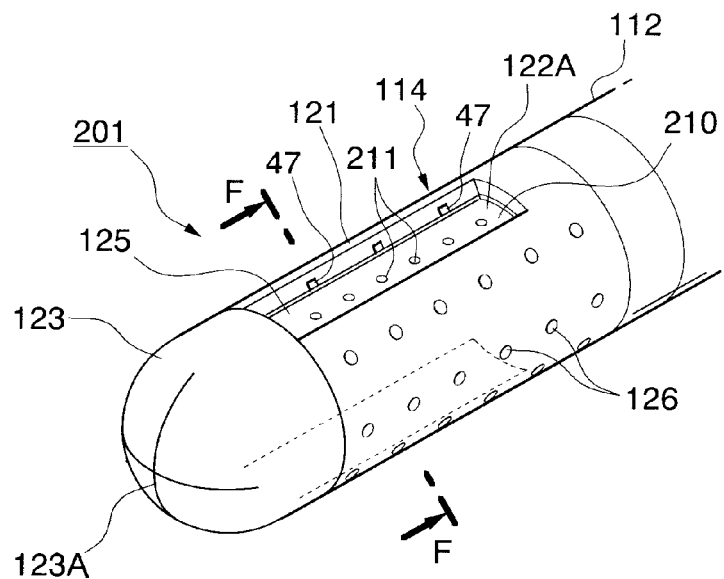
FIG. 43 is a perspective view of a cerclage instrument according to a seventh embodiment of the present invention.
Figure 44:
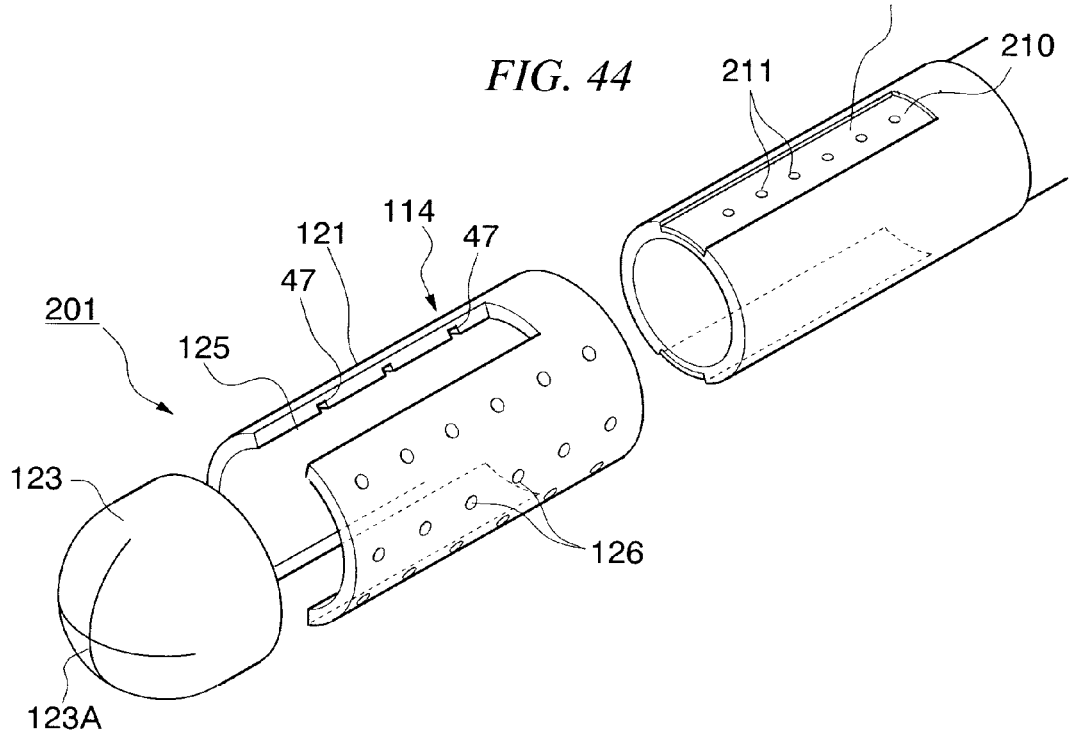
FIG. 44 is a perspective view according to the seventh embodiment of the present invention illustrating a disassembled state of the cerclage instrument shown in FIG. 43.

In a suture apparatus 201 illustrated in FIGS. 43 and 44, a therapy section 114 has a dual-pipe structure constituted by an outer cylinder 121 and a inner cylinder 122A. A pair of electrodes 210 are provided on an outer periphery of the inner cylinder 122A. The electrode 210 is formed elongated corresponding to the shape of the side hole 125 of the outer cylinder 121. A lumen is formed in the cylinder section 152 of the insertion section 112. The electrode 210 is connected to a connector 165 of the maneuvering section 113 through a conductive wire passed through the lumen in the cylinder section 152 (see FIG. 29). Furthermore, a plurality of suction holes 211 communicating to an inner hole of the inner cylinder 122A are formed on the electrode 210.

Figure 45:
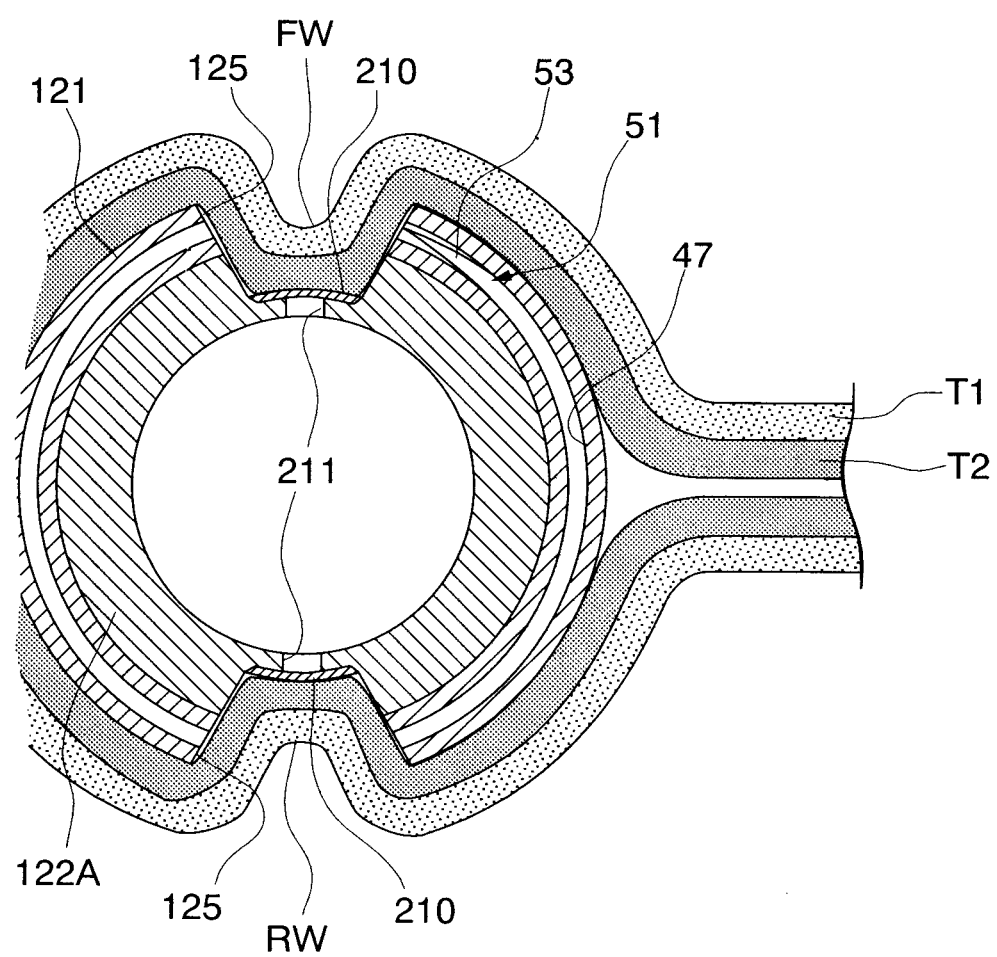
FIG. 45 is a cross-section viewed along F-F line shown in FIG. 43 illustrating the mucosa suctioned into the cerclage instrument according to the seventh embodiment of the present invention.

Suturing a tissue by using the suture apparatus 201 necessitates shrinking the stomach ST by using the looped section of the insertion section 112; and suctioning two points of the gastric wall, i.e., the anterior wall FW and the posterior wall RW through the side hole 125 and the suction holes 211. As illustrated in FIG. 45, the anterior wall FW and the posterior wall RW are brought into the side holes 125. Supplying electric current to the electrode 210 while maintaining the suctioned condition of the tissue damages the mucosa of the anterior wall FW and the mucosa of the posterior wall RW. Similarly to the above case, the spiral needle 51 is passed through the muscle coat of the anterior wall FW and the muscle coat of the posterior wall RW alternately to suture these tissues.

In the present embodiment, sutured tissues are adhered easily since the anterior wall FW and the posterior wall RW are sutured after damaging the mucosa by the electrode 210 built in the suture apparatus 201.

Eighth Embodiment

In an eighth embodiment, a spiral implant is embedded into a wall section of an organ, e.g., a stomach.

Figure 46:
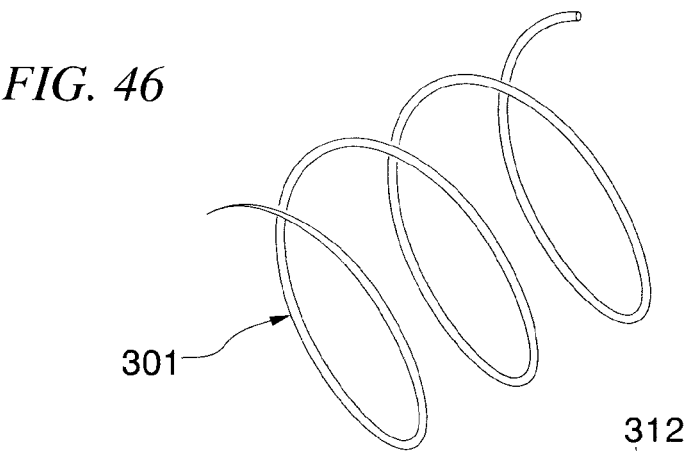
FIG. 46 is a perspective view illustrating an implant according to an eighth embodiment of the present invention.

As illustrated in FIG. 46, the implant 301 is produced from a material having biocompatibility, e.g., titanium, titanium alloy, stainless-steel, or hard resin. The distal end of the implant 301 is formed acute.

Figure 47:
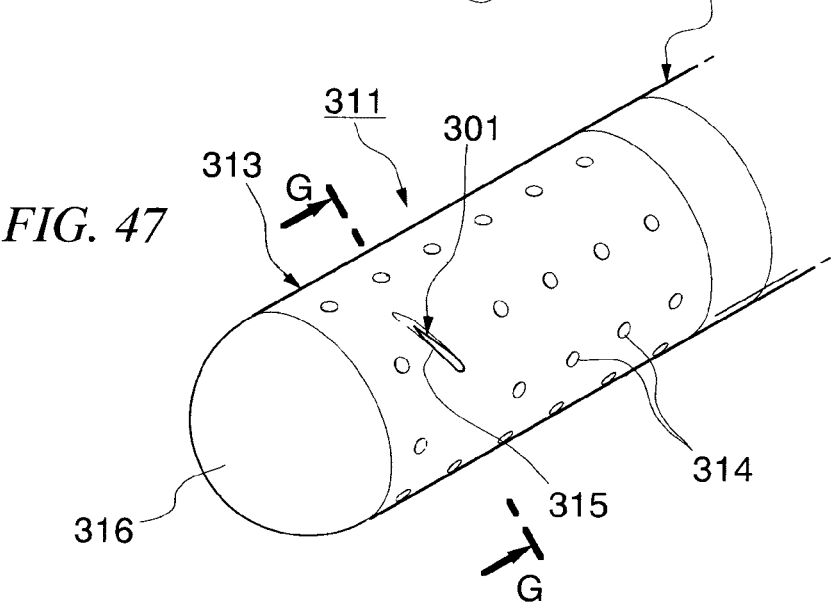
FIG. 47 is a perspective view illustrating a therapy section of a punching instrument according to the eighth embodiment of the present invention.

As illustrated in FIG. 47, a punching instrument 311 of the implant 301 has an insertion section 312 that is inserted through an overtube. The insertion section 312 has elasticity. A therapy section 313 is provided to the distal end of the insertion section 312. A plurality of suction holes 134 for suctioning tissue are formed on an outer periphery of the therapy section 313. An outlet 315 of the implant opens toward a substantial circumference at the distal end of the therapy section 313. An endoscope 2 can be inserted into the punching instrument 311. A transparent dome 316 is provided to the distal end of the therapy section 313. It should be noted that a slit may be formed to the dome 316 so that the endoscope 2 can project from the therapy section 313.

Figure 48:
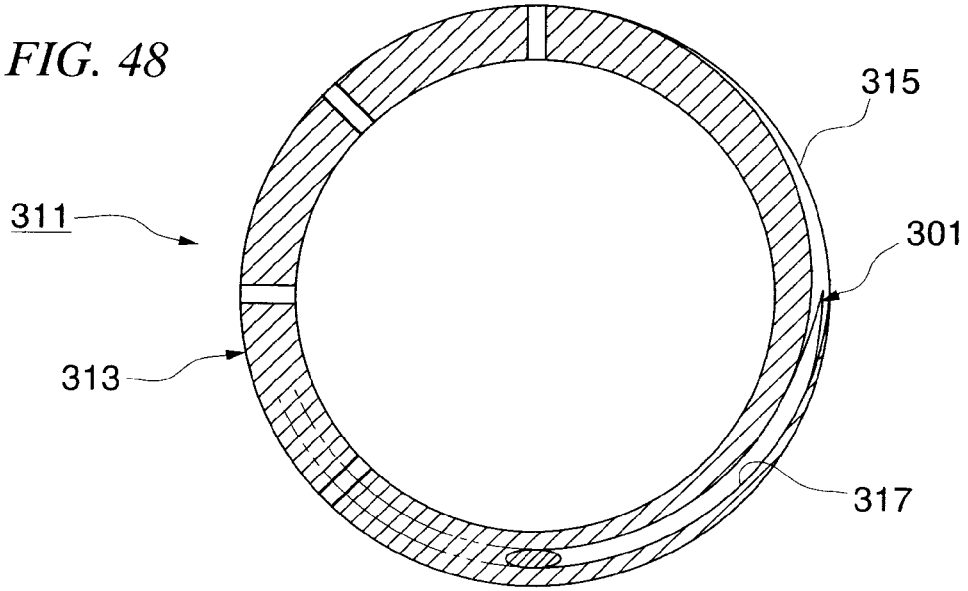
FIG. 48 is a cross-section of the cerclage instrument viewed along G-G line shown in FIG. 47 according to the eighth embodiment of the present invention.

As illustrated in FIG. 48, a spiral hole 317 that allows the implant 301 to be inserted therethrough is formed in the therapy section 313. The implant 301 can be pushed out by a pusher that is not shown in the drawing. The pusher is extracted through the insertion section 312 from a manipulation section that is disposed at a proximal end of the overtube.

Figure 49:
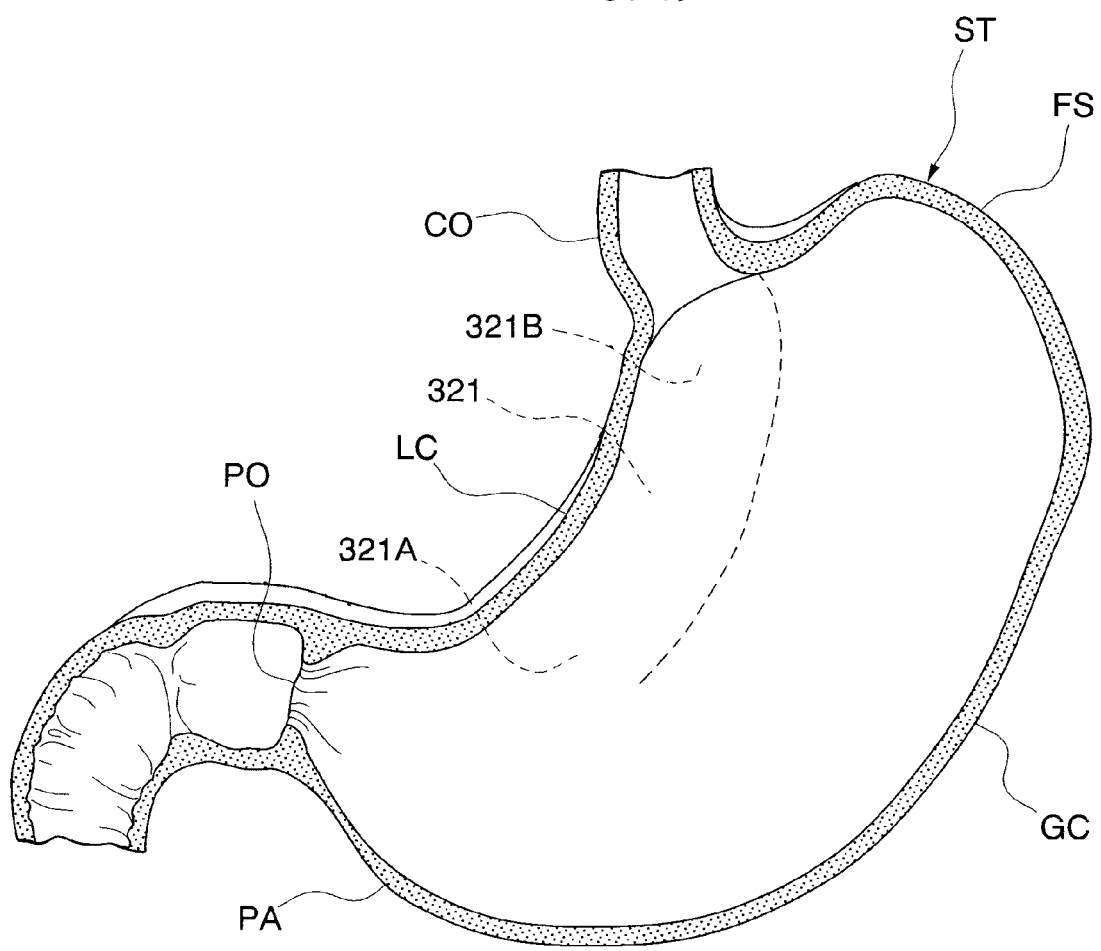
FIG. 49 is a perspective view illustrating an example of a position where the implant is embedded according to the eighth embodiment of the present invention.
Figure 50:
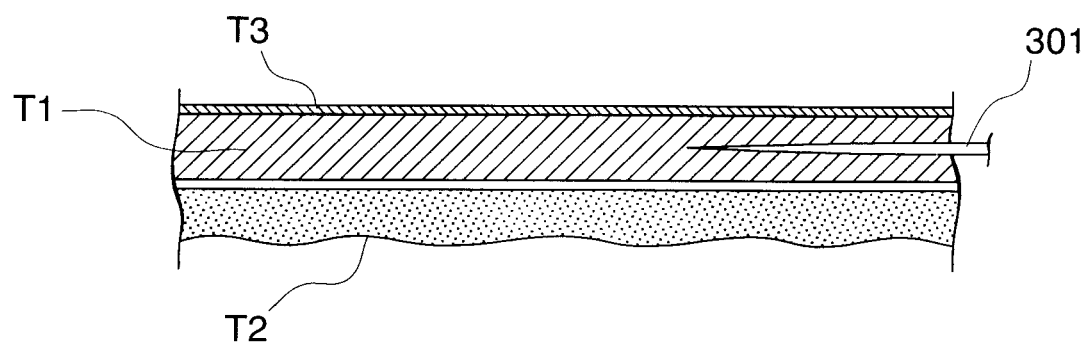
FIG. 50 is a perspective view illustrating how to embed the implant into a muscle coat according to the eighth embodiment of the present invention.
Figure 51:
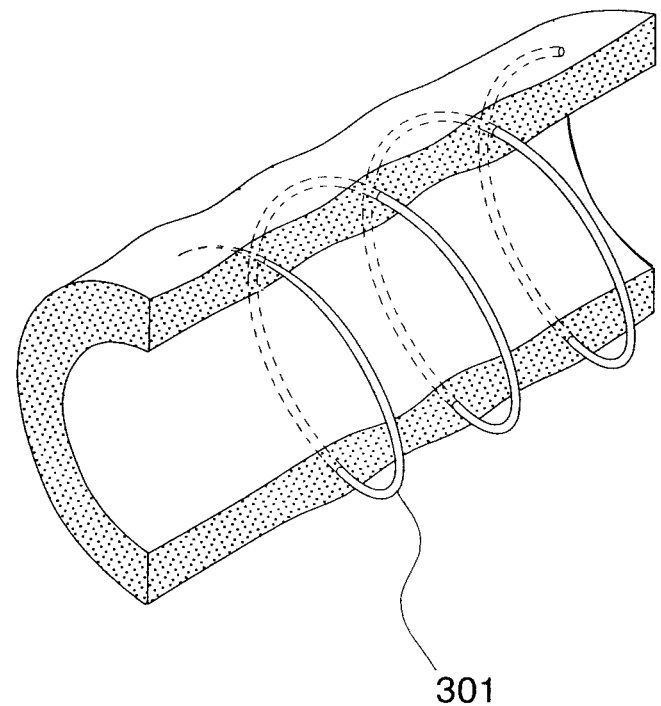
FIG. 51 is a perspective view illustrating the spirally embedded implant according to the eighth embodiment of the present invention.

The implant 301 is embedded after a part of the stomach ST is cerclaged according to the above-explained embodiments. As illustrated in FIG. 49, a therapy section 313 of the punching instrument 311 is introduced to an outlet 321A of a sleeve 321 formed by cerclaging a gastric wall, i.e., the therapy section 313 is introduced to a slightly ahead of the end section of the pylorus PO; and the implant 301 is pushed out from the outlet 315 by manipulating the manipulation section. As illustrated in FIG. 50, the acute distal end of the distal end of the implant 301 is pushed into the muscle coat T1; thus the implant 301 passing mainly through the muscle coat T1 is embedded in a tissue spirally since a diameter of the implant 301 is set to puncture a substantial midpoint of the muscle coat. As illustrated in FIG. 51, the outlet 321A of the sleeve 321 is reinforced by the implant 301 since the implant 301 is embedded into the tissue spirally. Similarly, the sleeve 321 is reinforced by embedding the implant 301 in the vicinity of the inlet 321B of the sleeve 321, i.e., by embedding the implant 301 in the vicinity of the cardia CO of the sleeve 321 or in the vicinity of the end section of the pylorus PO. Also, since a gap between the inlet 321B of the sleeve 321 and the cardia is blocked, the leak of food from the cardia to a main section of the stomach is prevented; thus it can contribute to enhance an effect in losing weight. The implant 301 may be embedded in a substantial whole area covering from the inlet 321B of the sleeve 321 to the outlet 321A.

In the present embodiment, it is possible to prevent the cerclaged section of the stomach from enlarging by embedding the implant 301 into the sleeve 321 formed by cerclaging the gastric wall. Also, fall-off of the implant 301 is prevented and the shape of the organ can be maintained by indwelling the implant 301 in the muscle coat T1. Furthermore, movement of the organ, e.g., contraction, enlargement, and peristalsis, etc. can be limited.

Figure 52:
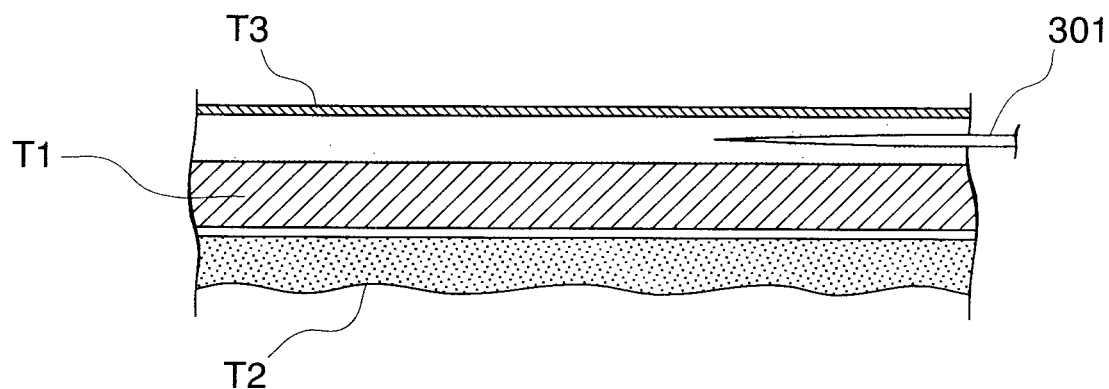
FIG. 52 is a perspective view illustrating how to embed the implant between a serous membrane and a muscle coat according to the eighth embodiment of the present invention.
Figure 53:
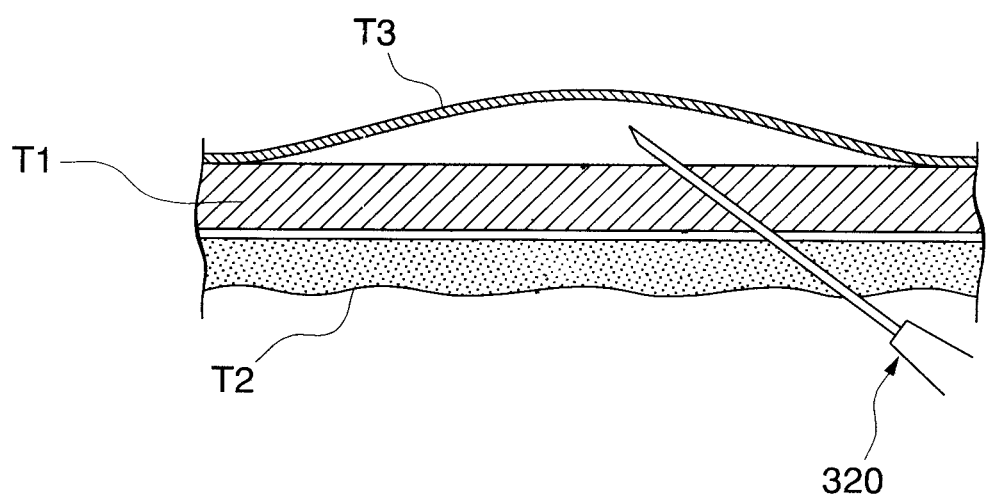
FIG. 53 is a perspective view illustrating pretreatment associated with embedding the implant between the serous membrane and the muscle coat according to the eighth embodiment of the present invention.

The implant 301 is indwelled in the muscle coat T1 or in the exterior thereof, but not in the mucosa T2. This is because the implant 301 indwelled in the mucosa T2 may sometimes fall off from the gastric wall. As illustrated in FIG. 52, normal saline solution may be injected between the muscle coat T1 and the serous membrane T3; and the implant 301 may be embedded between the muscle coat T1 and the serous membrane T3. As illustrated in FIG. 53, an injection needle 320 is used for injecting the normal saline solution. The injection needle 320 for this use is inserted through the endoscope 2.

Figure 54:
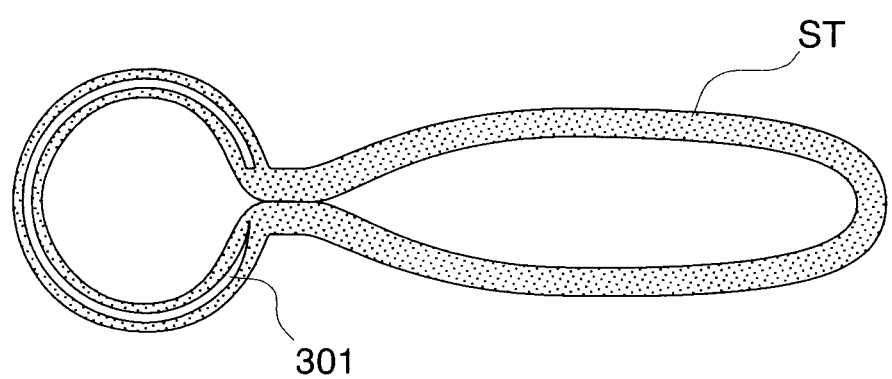
FIG. 54 illustrates an implant indwelled in a ring shape according to the eighth embodiment of the present invention.

As illustrated in FIG. 54, the implant 301 may form a ring. A sleeve may be formed by the ring implant 301 or by a spiral implant.

Figure 55:
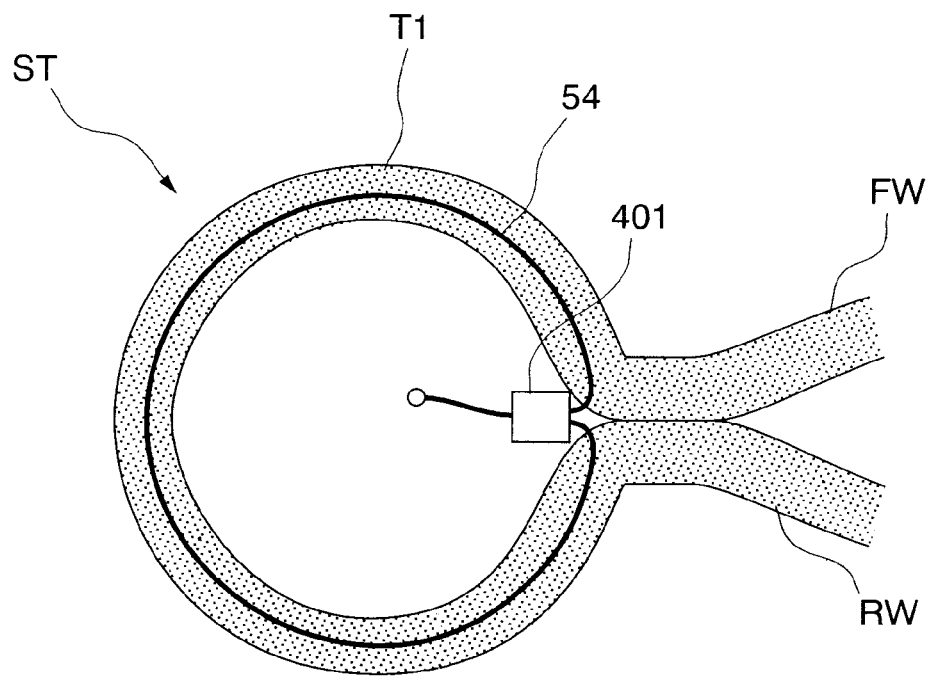
FIG. 55 illustrates a gastric wall sutured by a suture thread according to the eighth embodiment of the present invention.
Figure 56:
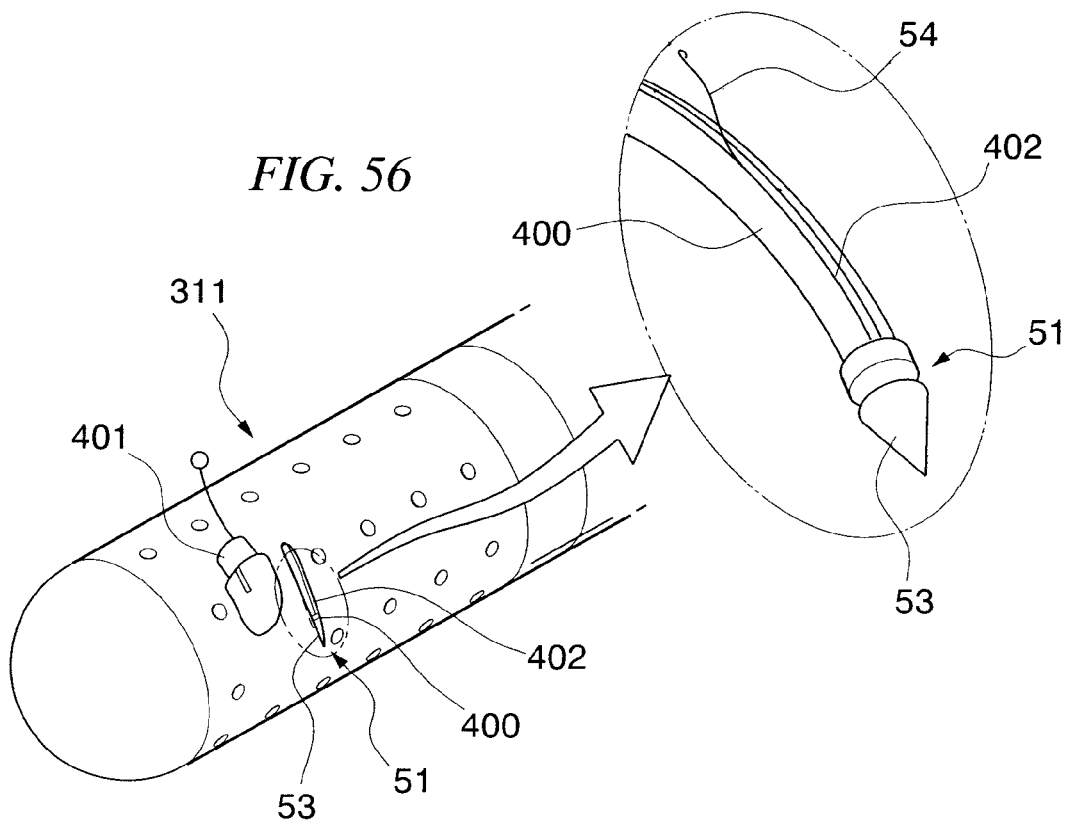
FIG. 56 is a perspective view illustrating a punching instrument, as an implant, using a suture thread according to the eighth embodiment of the present invention.
Figure 57:
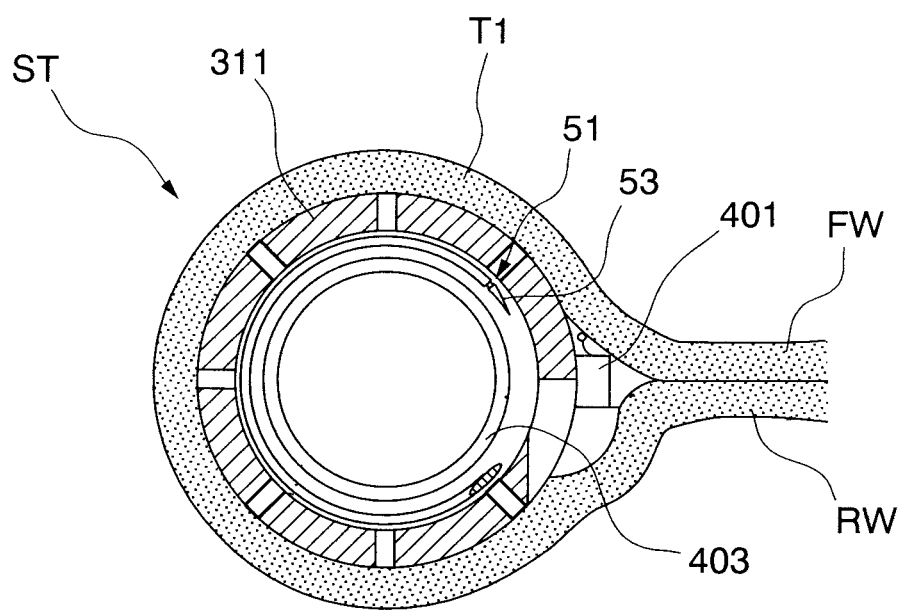
FIG. 57 is a perspective view illustrating an implant-punching instrument disposed in a stomach according to the eighth embodiment of the present invention.
Figure 58:
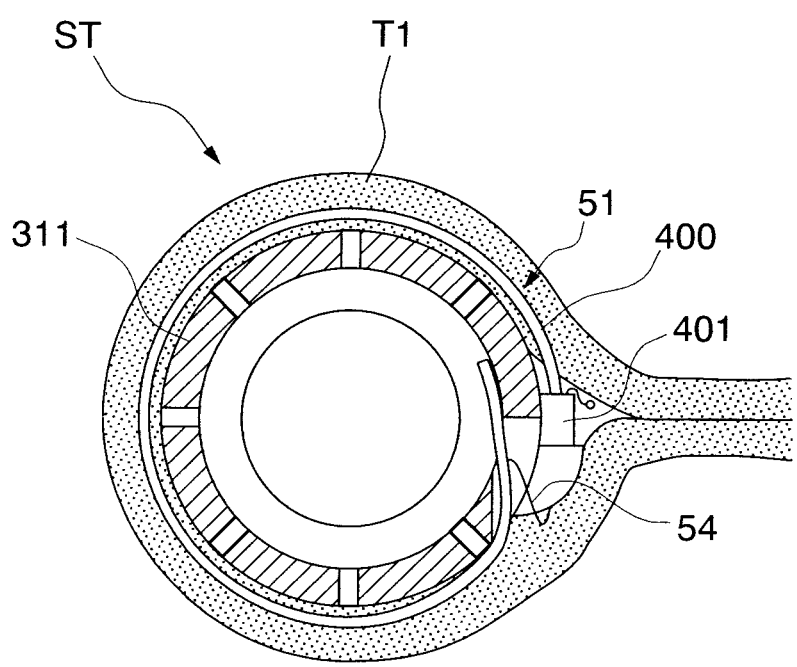
FIG. 58 is a perspective view illustrating a gastric wall punctured by a suture needle according to the eighth embodiment of the present invention.

As illustrated in FIG. 55, the shape of the muscle coat may be maintained by passing a thread through the muscle coat and suture the muscle coat. As illustrated in FIG. 56, a bending-needle 400 having a slit 402 may be provided to the punching instrument 311; and a needle distal end section 53 having a suture thread 54 attached thereto may be provided to the distal end of the bending-needle 400. The suture thread 54 disposed in the bending-needle 400 substantially in a round is passed through the stopper 401. The muscle coat T1 of the gastric wall is punctured by the bending-needle 400 rotated by a torque tube 403 while the gastric wall is suctioned as illustrated in FIG. 57. Upon disposing the bending-needle 400 in a substantial round, the distal end of the bending-needle 400 engages with the stopper 401 as illustrated in FIG. 58. Rotating the bending-needle 400 in the reverse direction causes the suture thread 54 to be removed from the bending-needle 400; thereby indwelling the suture thread 54 in the muscle coat T1. The gastric wall is sutured by binding the thread coming out of the stopper 401 by a forceps, etc. as illustrated in FIG. 55 since the suture thread 54 can move in only a direction due to the stopper 401.

Although the present invention has been described with respect to its preferred embodiments, the present invention is not limited to the embodiments described above. The configuration of the present invention allows for addition, omission, substitution and further replacement without departing from the spirit and scope of the present invention. The present invention is not limited to the above descriptions but is limited only by the appended claims.

What is claimed is:

1. A method for cerclaging suturing a gastric wall comprising:
    inserting a flexible elongated loop-forming member perorally into a stomach and advancing the loop-forming member such that the loop-forming member protrudes from a distal end portion of an overtube and advances along a lesser curvature line of the stomach toward a pyloric antrum of the stomach, wherein the loop-forming member is inserted through the overtube and the distal end portion of the overtube is located at a predetermined position near a cardia of the stomach;
    advancing the loop-forming member to contact with the gastric wall in vicinity of the pyloric antrum of the stomach, and then advancing the loop-forming member along a greater curvature line of the stomach such that the loop-forming member returns to the predetermined position and connects to the distal end portion of the overtube to form a closed loop in the stomach;
    suctioning air from the stomach after forming the closed loop member in the stomach such that an anterior gastric wall is in proximity with a posterior gastric wall within a region encircled by the closed loop; and
    suturing at least a portion of the anterior gastric wall to the posterior gastric wall that are in proximity in the region encircled by the closed loop.

2. The method for suturing the gastric wall according to claim 1, wherein a suture thread is punctured alternately through the anterior wall and the posterior wall while rotating a bent needle when the anterior gastric wall and the posterior gastric wall are sutured.

3. The method for suturing the gastric wall according to claim 2, further comprising:
    measuring thicknesses of a mucosa and a muscle coat of the gastric wall that should be sutured before or after inserting an instrument that sutures the anterior gastric wall and the posterior gastric wall;
    selecting the instrument suitable for the measured thicknesses of the mucosa and the muscle coat, and suturing the mucosa of the gastric wall by using the instrument.

4. The method for suturing the gastric wall according to claim 3, wherein the thicknesses of the mucosa and the muscle coat of the gastric wall are measured by using an ultrasonic endoscope or an ultrasonic searcher attached to the instrument.

5. The method for suturing the gastric wall according to claim 2, further comprising:
    measuring thicknesses of a mucosa and a muscle coat of the gastric wall that should be sutured before or after inserting an instrument that sutures the anterior gastric wall and the posterior gastric wall; and
    adjusting the instrument based on the measured thicknesses of the mucosa and the muscle coat, and suturing the mucosa of the stomach by using the instrument.

6. The method for suturing the gastric wall according to claim 5, wherein the thicknesses of the mucosa and the muscle coat of the gastric wall are measured by using an ultrasonic endoscope or an ultrasonic searcher attached to the instrument.

7. The method for suturing the gastric wall according to claim 1, including dissecting mucosa of tissues of the gastric wall before suturing the anterior gastric wall and the posterior gastric wall.

8. The method for suturing the gastric wall according to claim 1, including embedding an implant into a sleeve portion of the stomach, wherein the sleeve portion of the stomach is formed by the suturing.

9. The method for suturing the gastric wall according to claim 8, wherein a position for embedding the implant is at an entrance of the sleeve portion of the stomach in vicinity of the cardia of the stomach; at an exit of the sleeve portion of the stomach in vicinity of a pylorus of the stomach; or at least a part of the sleeve portion of the stomach.

10. The method for suturing the gastric wall according to claim 8, wherein the implant is a metal or resin coil, or a suture thread.

* * * * *